US006994960B1

(12) United States Patent
Foote et al.

(10) Patent No.: US 6,994,960 B1
(45) Date of Patent: Feb. 7, 2006

(54) NUCLEIC ACID DIAGNOSTICS BASED ON MASS SPECTROMETRY OR MASS SEPARATION AND BASE SPECIFIC CLEAVAGE

(75) Inventors: Simon Foote, Fairfield (AU); Colleen Elso, Northcote (AU); Richard Simpson, Richmond (AU); Gavin Reid, Essendon (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 09/424,629

(22) PCT Filed: May 28, 1998

(86) PCT No.: PCT/AU98/00396

§ 371 (c)(1),
(2), (4) Date: Mar. 13, 2000

(87) PCT Pub. No.: WO98/54571

PCT Pub. Date: Dec. 3, 1998

(30) Foreign Application Priority Data

| May 30, 1997 | (AU) | PO 7109 |
| May 28, 1997 | (AU) | PO 7102 |
| Feb. 5, 1998 | (AU) | PP 1665 |
| May 19, 1998 | (AU) | PP 3592 |

(51) Int. Cl.
| C12Q 1/68 | (2006.01) |
| C12N 15/00 | (2006.01) |
| C12N 15/63 | (2006.01) |
| C12N 1/20 | (2006.01) |
| C07H 21/04 | (2006.01) |

(52) U.S. Cl. ............... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search ............... 435/6, 435/91.1, 91.2, 91.21, 91.3, 196; 536/24.3, 536/23.1; 935/6, 77; 436/518, 94; 250/282, 250/288
See application file for complete search history.

(56) References Cited

U.S. PATENT DOCUMENTS

| 4,862,358 A | * | 8/1989 | Kimura | 364/413 |
| 5,808,300 A | * | 9/1998 | Caprioli | 250/288 |
| 5,869,242 A | | 2/1999 | Kamb | 529/879 |
| 5,985,619 A | * | 11/1999 | Sutherland et al. | 435/91.2 |
| 6,074,823 A | * | 6/2000 | Koster | 435/6 |

FOREIGN PATENT DOCUMENTS

WO    WO 97/03210    1/1997

OTHER PUBLICATIONS

Richard G. H. Cotton, et al. (1988), "Reactivity of cytosine and thymine in single–base–pair mismatches with hydroxylamine and osmium tetroxide and its application to the study of mutations", *Proceedings of the National Academy of Sciences of the U.S.A.*, 85: 4397–4401.

M. Hattori, et al., (1993), "Orphan Peak Analysis: A Novel Method for Detection of Point Mutations Using an Automated Fluorescence DNA Sequencer", *Genomics*, 15: 415–417.

R.J. Lipshutz, et al., (1995), "Using Oligonucleotide Probe Arrays to Access Genetic Diversity", *Bio Techniques*, 19: 442–447.

R.J. Lipshutz, et al., (1995), "Using Oligonucleotide Probe Arrays to Access Genetic Diversity", *Bio Techniques*, 19: 442–447.

E. Nordhoff, et al. (1992), "Matrix–assisted Laser Desorption/Ionization Mass Spectrometry of Nucleic Acids with Wavelengths in the Ultraviolet and Infrared", *Rapid Communications in Mass Spectrometry*, 6: 771–776.

M. Orita, et al. (1989), "Detection of polymorphisms of human DNA by gel electrophoresis as single–strand conformation polymorphisms", *Proceedings of the National Academy of Sciences of the U.S.A,86*: 2766–2770.

S.C. Pomerantz, et al. (1993), "Determination of Oligonucleotide Composition from Mass Spectrometrically Measured Molecular Weight", *American Society for Mass Spectrometry*, 4: 204–209.

Hahner, S., et al. (1997), "Matrix–Assisted Laser Desorption/Ionization Mass Spectrometry (MALDI) of endonucleae digests of RNA", *Nucleic Acids Research*, 25(10): 1957–1964.

(Continued)

Primary Examiner—Jeffrey Fredman
Assistant Examiner—Arun Chakrabarti
(74) Attorney, Agent, or Firm—Scully, Scott, Murphy & Presser

(57) ABSTRACT

A method of detecting a mutation or a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-ATOF MS and/or other equivalent procedure to produce a fingerprint of then oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

20 Claims, 13 Drawing Sheets

OTHER PUBLICATIONS

Liu, Yan–Hui, et al (1995) "Rapid Screening of Genetic Polymorphisms Using Buccal Cell DNA with Detection by Matrix–assisted Laser Desorption/Ionization Mass Spectrometry", *Rapid Communications in Mass Spectrometry*, 9:735–743.

Taranenko, N. I., et al. (1996) "Laser desorption mass spectrometry for point mutation detection", *Genetic Analysis: Biomolecular Engineering*, 13: 87–94.

Nordhoff, E., et al. (1996) "Mass Spectrometry Of Nucleic Acids", *Mass Spectrometry Reviews*, 15(2): 67–138.

Talbo, G., et al. (1996) "Aspects of the Sequencing of Carbohydrates and Oligonucleotides by Matrix–assisted Laser Desorption/Ionization Post–source Decay", *Rapid Communications in Mass Spectrometry*, 10(1): 100–103.

Kaufmann, R., et al. (1996) "Post–source Decay and Delayed Extraction in matrix–assisted Laser Desorption/ Ionization–Reflectron Time–of–Flight Mass Spectrometry. Are there Trade–offs?", *Rapid Communications in Mass Spectrometry*, 10: 1199–1208.

* cited by examiner

CAC AAC GGA ATA GAC CCA AAA AGA UAA UUU CUA UCU
GUG UUG CCU UAU CUG GGU UUU UCU AUU AAA GAU AGA

GAU UUG CUU UAA AAC GUU UUU UUA GGA UCA CAA UGA
CUA AAC GAA AUU UUG CAA AAA AAU CCU AGU GUU ACU

UAU CUU UGC UGU AUU UGU AUA GUU CGA UGC UAA AUG
AUA GAA ACG ACA UAA ACA UAU CAA GCU ACG ATT TAC
*

CUC AUU GAA ACA AUC A
GAG TAA CTT TGT TAG T

FIG 4

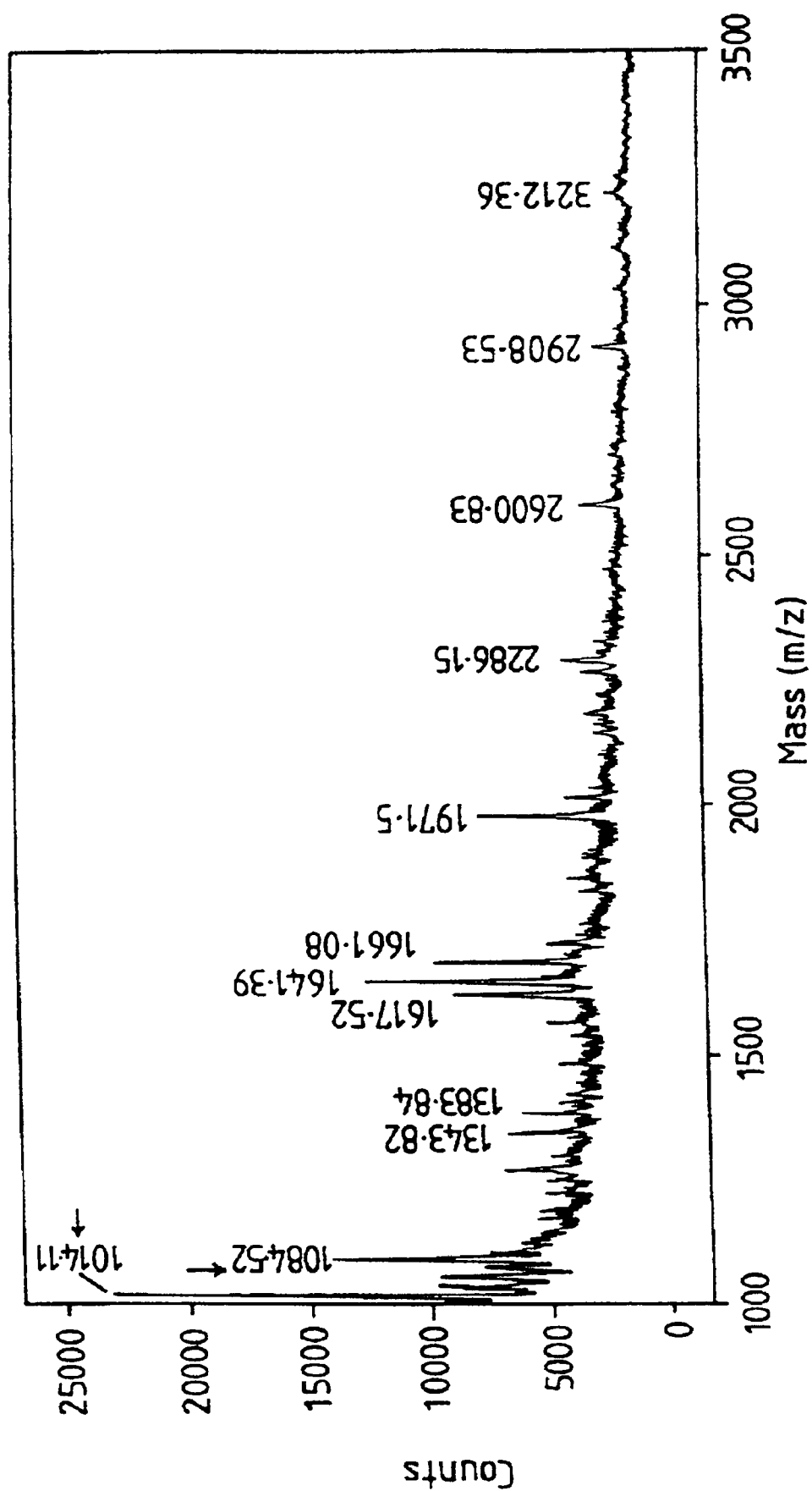
FIG 5B(i)a

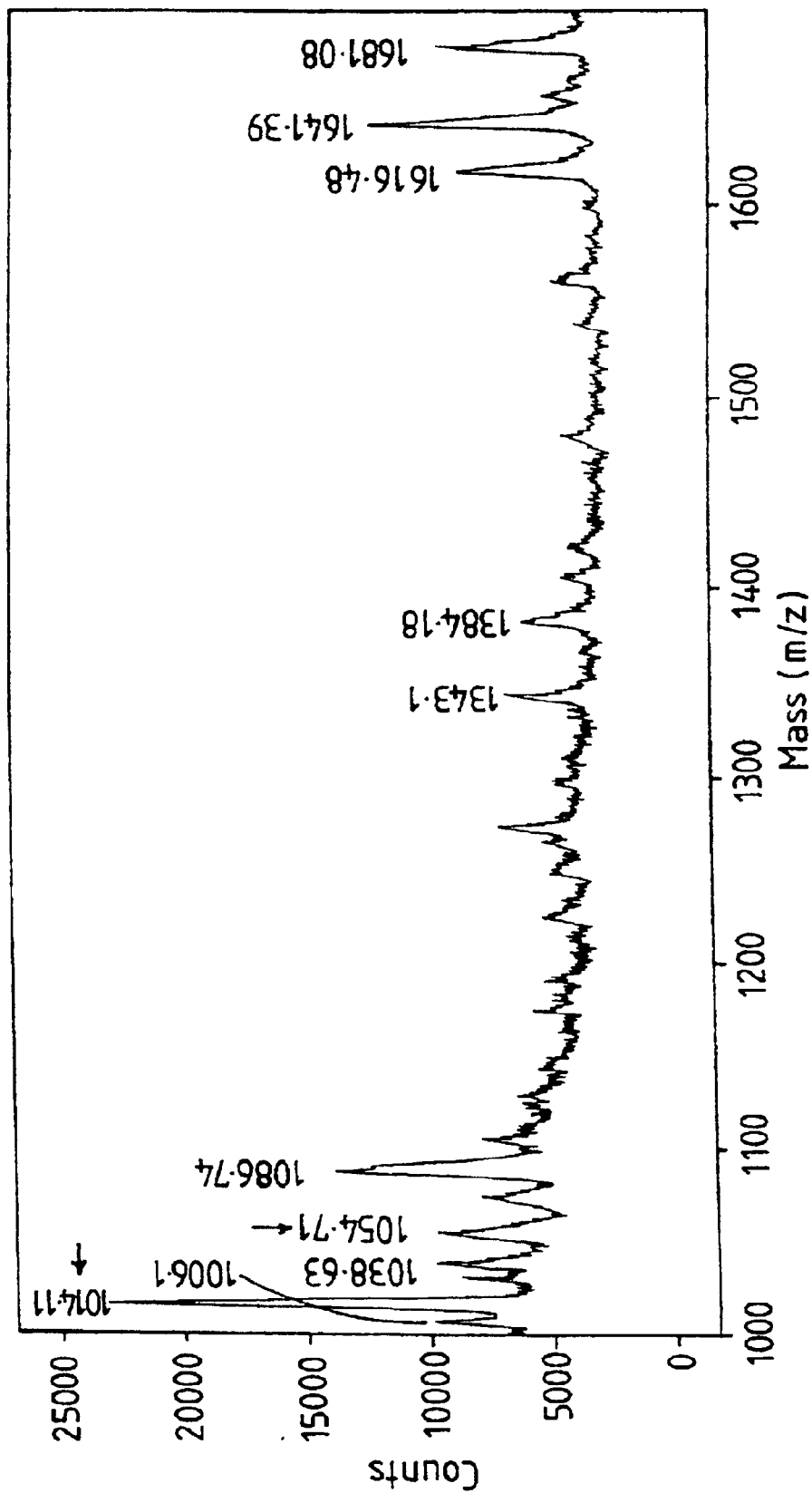
FIG 5B(i)b

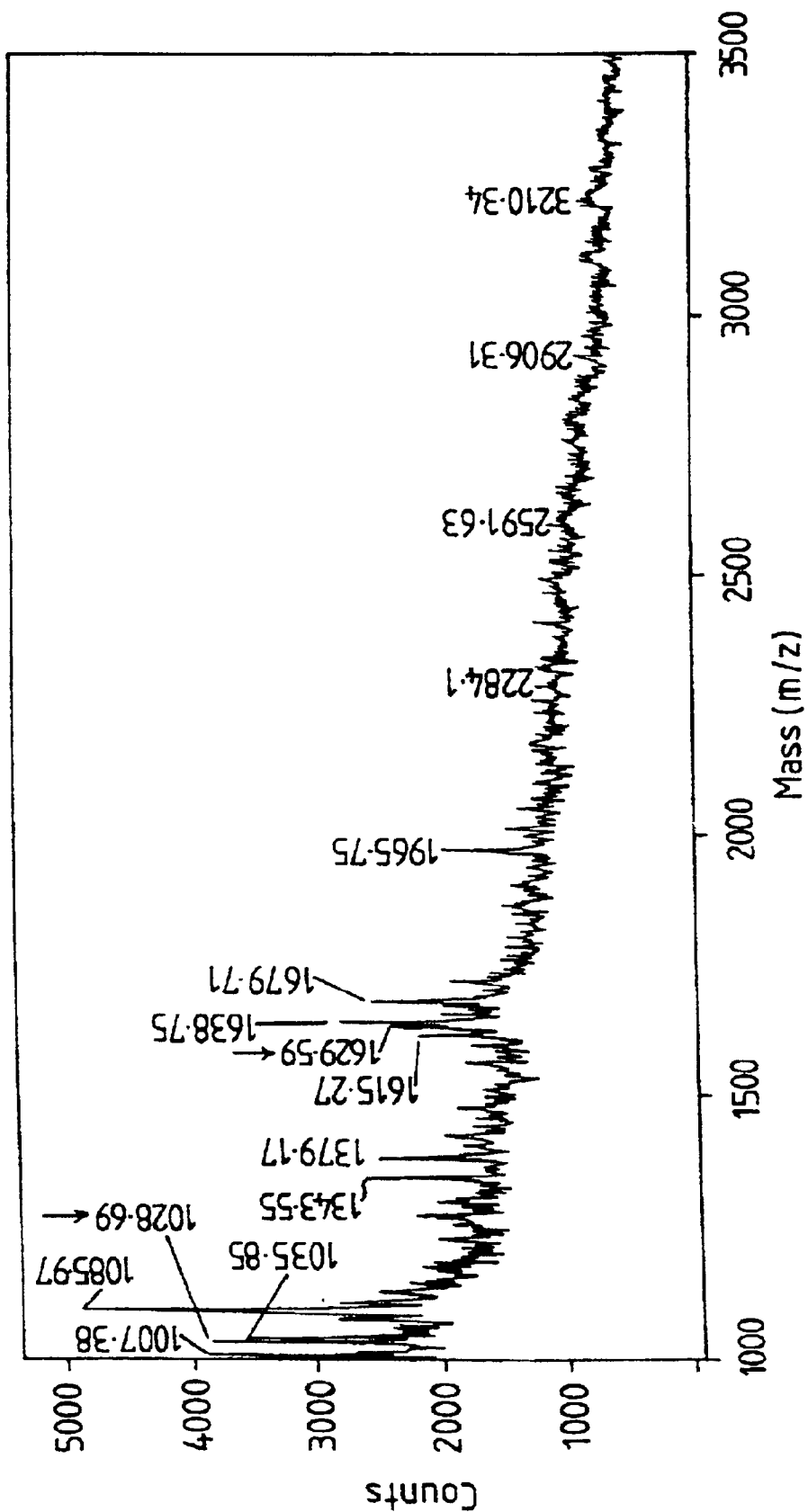
FIG 5B(ii)a

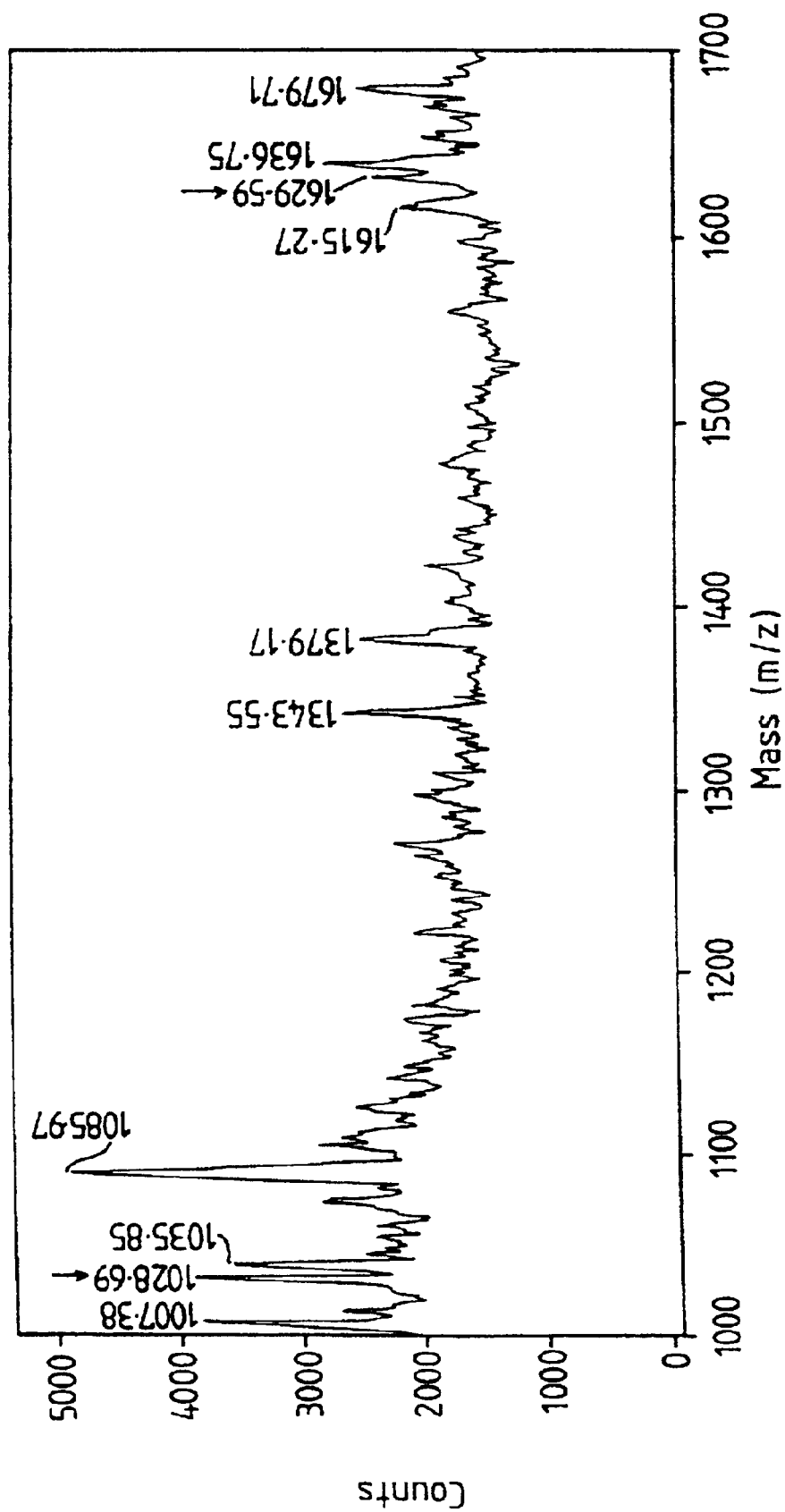
FIG 5B(ii)b

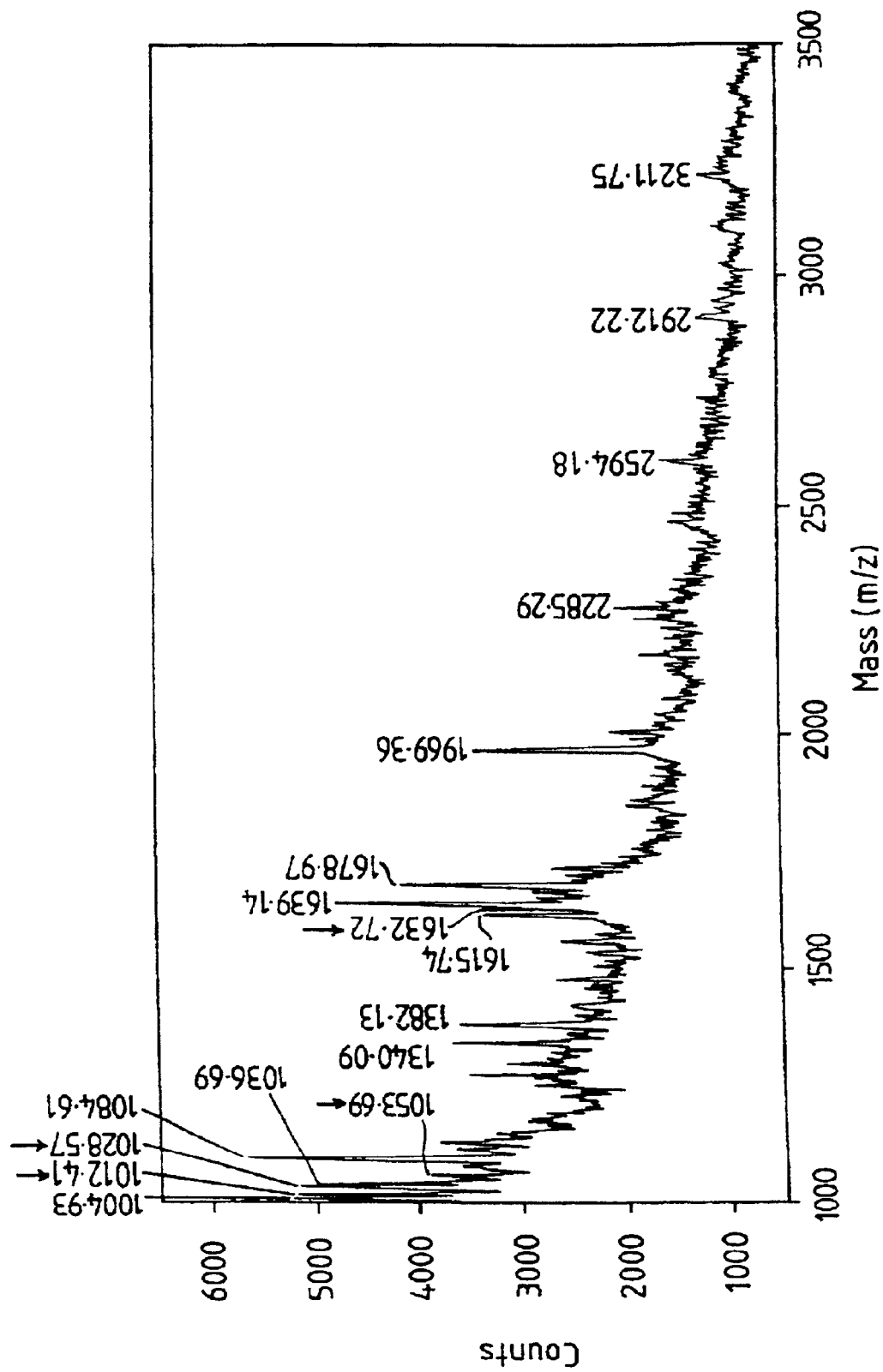
FIG 5B(iii)a

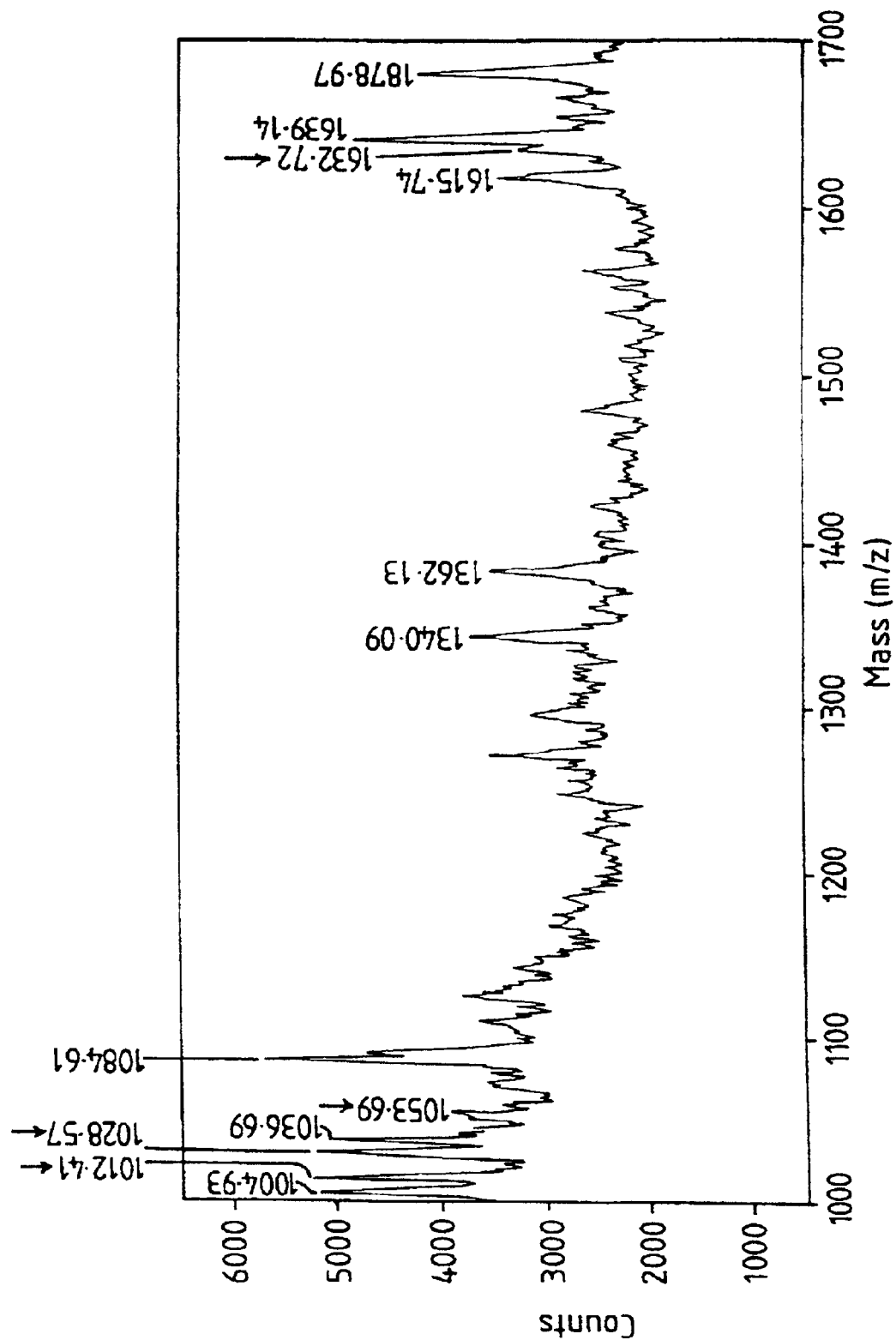
FIG 5B(iii)b

NUCLEIC ACID DIAGNOSTICS BASED ON MASS SPECTROMETRY OR MASS SEPARATION AND BASE SPECIFIC CLEAVAGE

FIELD OF THE INVENTION

The present invention relates generally to a method for detecting a mutation in a nucleic acid molecule. The method of the present invention does not require prior knowledge of a reference or wild-type nucleotide sequence nor does it require a gel electrophoresis step. The method of the present invention is particularly useful in identifying mutations and polymorphisms in genomic DNA and more particularly in the human genome and to determine and/or confirm the nucleotide sequence of target nucleic acid molecules. The method of the present invention may also be automated.

BACKGROUND OF THE INVENTION

Bibliographic details of the publications referred to by author in this specification are collected at the end of the description.

The increasing sophistication of recombinant DNA technology is greatly facilitating research and development in a range of biotechnological fields. A particularly important area is the generation of nucleotide mutants and the screening for and identification of such mutants. This in turn has implications, for example, in understanding the genetic basis behind certain disease conditions which is becoming of increasing relevance as the human genome is progressively sequenced.

An efficient and accurate method of mutation detection is crucial in implicating disease candidate genes and in the screening programs which follow identification of disease causing mutations. Many human inherited and sporadic disorders are caused by small mutations including base substitutions, additions and deletions. Among these disorders are the Mendelian single gene disorders, sporadic somatic mutations causing cancers and complex genetic traits. Whilst some diseases are caused by a limited and well characterised set of mutations, most genetic diseases are caused by one or more of a large range of mutations occurring anywhere within the gene. It is important, therefore, that a mutation detection protocol be able to scan a region of DNA, identify any change and describe the resulting nucleotide differences from wild-type. With the increasing use of population molecular genetics and as clinicians begin to use mutation analysis as a clinical tool, there is a need to develop mutation detection protocols which can be automated, are less dependant on user expertise and are more accurate and reliable.

Current mutation detection protocols require either a gel based detection system or sequence specific primers. Gel based detection methods include direct sequencing of amplified DNA fragments and various techniques involving either cleavage of mismatched bases in heteroduplexes or mobility differences of single or partially denatured DNA strands.

Detection of mutations by DNA sequencing can provide good results in relation to accuracy and information about the position and nature of the mutation (Hattori et al, 1993), however, although advances have been made in this area, the technique is not fully automated and is labour intensive. Most mutations occur as heterozygotes and there are technical difficulties with the ability of currently available computer software to identify two different nucleotide bases at a mutated residue.

Many mutation detection techniques exploit differential electrophoretic mobilities of DNA fragments with sequence differences. Single strand conformation polymorphism (SSCP) exploits the fact that the secondary structure of a single strand of DNA is sequence based and, therefore, strands with even just one base difference will migrate at a different rate (Orita et al, 1989). This technique is again gel based and can lack sensitivity. Furthermore, the method cannot be readily automated and requires a large amount of labour due to the necessary gel step which in most cases must be optimised to the specific sample being analysed. They also do not give any information about the position or nature of the change and do not routinely identify all mutations.

Mutation detection based on the identification of base pair mismatches in heteroduplex DNA strands is another method of identifying point changes. There are a number of techniques available that cleave DNA at mismatched base pairs in heteroduplex DNA. Mismatch cleavage protocols include chemical and enzymatic mismatch cleavage. The techniques are also gel based. The chemical cleavage method uses osmium tetroxide to cleave at the mismatched base (Cotton et al, 1988) followed by separation of cleaved products on denaturing gels. A major disadvantage of the chemical cleavage protocol is the use of extremely toxic chemicals.

Other methods for detection of known mutations include minisequencing allele specific polymerase chain reaction (PCR), oligonucleotide probe arrays (Lipshutz et al, 1995) which requires knowledge of the sequence of wild-type and mutant. Although this technique is suitable for non-gel based detection methods, it is only useful for know mutations. Furthermore, the large number of oligonucleotides required to cover all known mutations in many genes makes this approach prohibitively expensive and labour intensive.

With the development of the matrix assisted laser desorption ionisation—time of flight mass spectrometer (MALDI-TOF MS), the ability to accurately determine the mass of biomolecules of a limited size has been achieved. Although detection of DNA fragments of up to 622 base pairs in length has been reported, large fragments cannot be accurately sized and a mass accuracy of ±3 bp is quoted (Liu et al, 1995). This level of accuracy is clearly insufficient for the detection and characterisation of base substitutions.

There is a need, therefore, to develop an effective and accurate means of detecting mutations in nucleic acid molecules. Preferably, the mutation detection system would be automatable.

In work leading up to the present invention the inventors developed a mutation detection system which exploits the accuracy of mass determination of MALDI-TOF MS and which is applicable for large DNA fragments. The method of the present invention do not require gel electrophoresis nor is prior knowledge of the nucleotide sequence necessary. The method of the present invention is also capable of being automated.

SUMMARY OF THE INVENTION

Sequence Identity Numbers (SEQ ID NOs.) for the nucleotide and amino acid sequences referred to in the specification are defined following the bibliography.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention contemplates a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Another aspect of the present invention provides a method of detecting a difference of one or more nucleotides between a nucleic acid molecule to be tested and a reference nucleic acid molecule, said method comprising amplifying said test nucleic acid molecule by polymerase chain reaction (PCR), subjecting the test amplified nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Yet another aspect of the present invention is directed to a method of detecting a difference of one or more nucleotides between a nucleic acid molecule to be tested and a reference nucleic acid molecule, said method comprising amplifying said test nucleic acid molecule by PCR, subjecting the test amplified nucleic acid molecule to base specific cleavage to generate oligonucleotide fragments of from about 2 to about 1000 bases, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Still yet another aspect of the present invention relates to a method of detecting a difference of one or more nucleotides between a nucleic acid molecule to be tested and a reference nucleic acid molecule, said method comprising amplifying said test nucleic acid molecule and incorporating uracil residues, subjecting the test amplified nucleic acid molecule to uracil specific cleavage mediated by a uracil-N-glycosylase to generate oligonucleotide fragments of from about 2 to about 1000 bases, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Another aspect of the present invention contemplates a computer programme capable of controlling a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Yet another aspect of the present invention is directed to an apparatus capable of detecting a difference of one or more nucleotides between a nucleic acid molecule to be tested and a reference nucleic acid molecule, said apparatus comprising means of subjecting the test nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Still another aspect of the present invention provides a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS and/or other equivalent procedure and subjecting said separated fragments to further separation means, such as post source decay (PSD) or other similar technique, to separate fragmentation products to generate a spectrum dependent on nucleotide sequence and then identifying an altered peak relative to a reference nucleic acid molecule subjected to the same procedure wherein the presence of an altered peak is indicative of a difference of one or more nucleotides in said tested nucleic acid molecule.

BRIEF DESCRIPTION OF THE FIGURES

FIG. 2 is a graphical representation showing mass spectrogram of reacted, separated products of normal TUB which represents a homozygote. Mode: linear; Accelerating Voltage: 20,000; Grid Voltage: 92.000%; Guide Wire Voltage 0–100%; Delay 125ON; Laser:1800; Scans Averaged: 128; Pressure: 9.94e-07; Low Mass Gate: 900.0; Negative Ions: ON.

FIG. 3 is graphical representation showing mass spectrogram of reacted, separated products of both TUB-M and TUB which represents a heterozygote. Mode: linear, Accelerating Voltage: 20,000; Grid Voltage: 92.000%; Guide Wire Voltage 0–100%; Delay 125ON; Laser:1800; Scans Averaged: 128; Pressure: 1.89e-06; Low Mass Gate 900.0; Negative Ions: ON.

FIG. 4 is a representation of the nucleotide sequence of IL-12 untranslated region PCR product used in Example 13. Primers are shown in bold. Expected cleavage products >2 bp are underlined. The polymorphism is at position 97 and is indicated by asterisk. The polymorphism is a C to T change which results in a change of the cleavage products at that position from CGA to AGA in the forward strand and CAAGC to CAA in the reverse stand. The presence of C at position 97 results in a TaqI site and this allele is called "+", the other allele is respectively "−".

FIGS. 5B—5G are graphical representations showing linear MALDI-TOF spectra of cleavage products. The spectra on the left show a mass range of 1000 to 3500 and those on the right are the same spectra but show in detail the mass range from 1000 to 1700. Spectra 5B and 5C are from a −/− individual spectra 5D and 5E are from a +/+ individual, and spectra 5F and 5G are from a +/− individual. Observed masses are indicated above peaks. Arrows show the peaks that change between the two alleles.

DETAILED DESCRIPTION OF THE PREFERRED EMBODIMENTS

Figure 1:
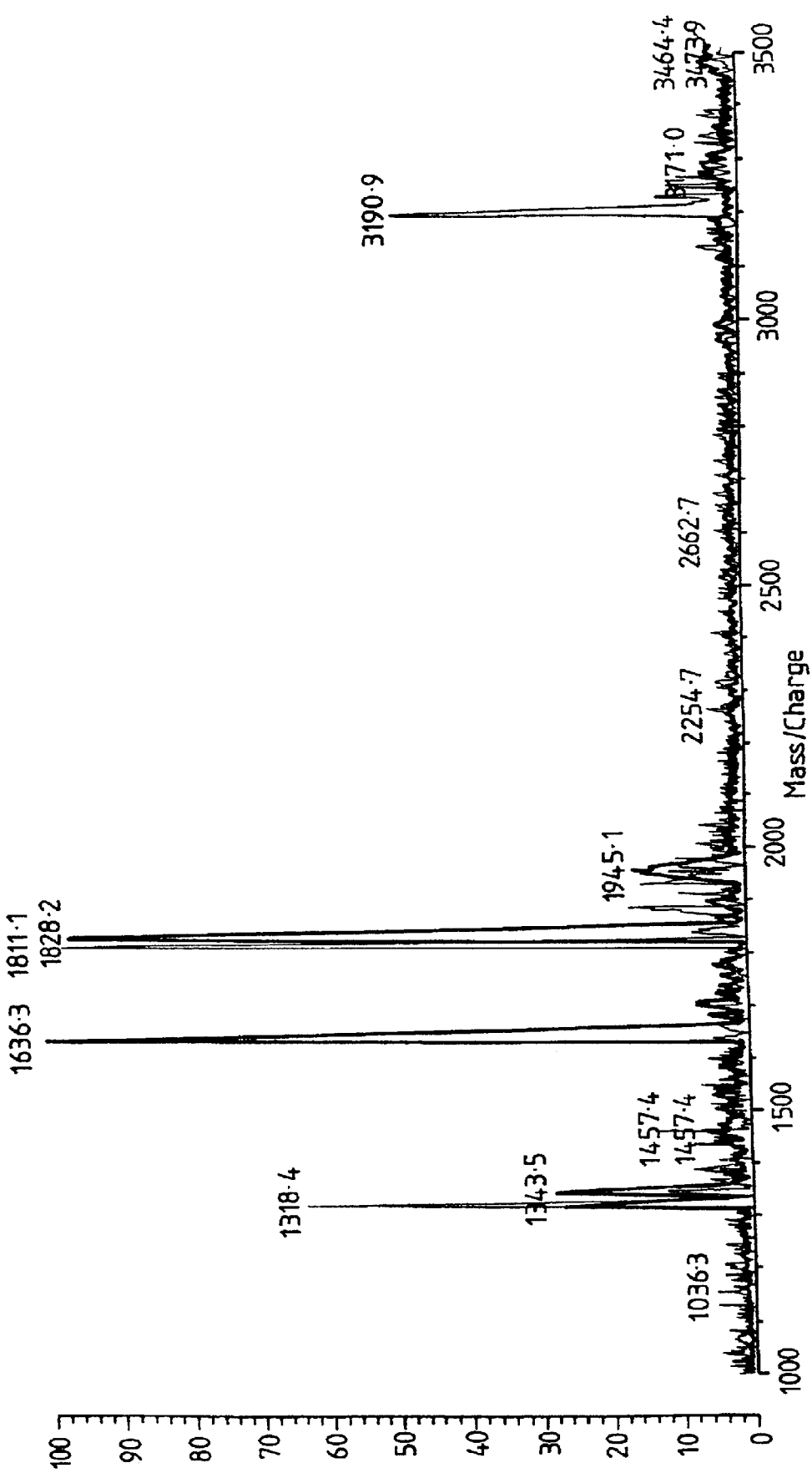
FIG. 1 is a graphical representation showing mass spectrogram of cleavage products of two oligonucleotides, 1 and 2, which differ at two nucleotides, one produces a fragment with a different nucleotide composition and the other introducing a new cleavage site. The two line thicknesses represent the overlaid tracings of the two different oligonucleotides. 1636.3 represents a thick line peak and 3190.9 represents a thin line peak. 1811.1 is a thin line peak and 1828.2 is a thick line peak. Kratos Kompact MALDI 4v51.2; % int. 100%=24 mV (thin); 81 mV (thick).

The present invention is predicated in part on a base specific cleavage reaction to generate a set of small oligonucleotides bounded by the base cleaved. The nucleic acid molecule may be completely or only partially cleaved or digested. These fragments are then separated based on mass by MALDI-TOF MS. This generates a fingerprint of the nucleic acid fragment comprising a series of peaks where each peak represents the mass of each small cleavage product. As a result of the sensitivity of mass determination, each oligonucleotide of given length but different nucleotide composition produces a different mass. The mass of each peak, therefore, corresponds to the nucleotide composition of the fragment as well as to its length. Consequently, any nucleotide substitution results in either a shifted peak due to the mass difference in the new cleavage fragment or, if the mutation changes the targeted base, a cleavage product containing a different number of bases.

Accordingly, one aspect of the present invention contemplates a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Conveniently, screening is carried out by comparing the cleavage product masses of the reference or wild-type nucleic acid to those of the test sample. Mass changes corresponding to base changes are readily observed.

Accurate mass determination of these small fragments is possible allowing unambiguous assignation of base composition of each oligonucleotide. This knowledge allows deduction of the nature of the mutation and, after specific cleavage at different bases and integration of the data, the position of the mutation.

The method of the present invention is applicable to any nucleic acid molecule such as but not limited to DNA, genomic DNA, cDNA, plasmid DNA, satalite DNA, mRNA and other RNA molecules as well as DNA:DNA, DNA:RNA and RNA:RNA hybrids. The present invention is particularly applicable to nucleic acid molecules amplified by, for example, polymerase chain reaction (PCR).

According to this aspect of the present invention, there is provided a method of detecting a difference of one or more nucleotides between a nucleic acid molecule to be tested and a reference nucleic acid molecule, said method comprising amplifying said test nucleic acid molecule by polymerase chain reaction (PCR), subjecting the test amplified nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

A particularly preferred requirement is that the source of nucleic acid is cleavable to oligonucleotide fragments of from 2 bases to 1000 bases, preferably of from 3 bases to 500 bases, more preferably of from 4 bases to 100 bases and even more preferably of from 4 bases to 50 bases. Oligonucleotide fragments of form 4 bases to 40 bases are of particular usefulness in practising the present invention.

Accordingly, the present invention is directed to a method of detecting a difference of one or more nucleotides between a nucleic acid molecule to be tested and a reference nucleic acid molecule, said method comprising amplifying said test nucleic acid molecule by PCR, subjecting the test amplified nucleic acid molecule to base specific cleavage to generate oligonucleotide fragments of from about 2 to about 1000 bases, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

The nucleic acid may be cleaved by a range of chemical molecules including enzymes. Enzymes are particularly preferred due to their specificity. One useful enzyme is uracil-N-glycosylase which cleaves DNA at uracil residues incorporated, for example, during a PCR. However, a range of enzymes may be employed.

According to this embodiment, the present invention relates to a method of detecting a difference of one or more nucleotides between a nucleic acid molecule to be tested and a reference nucleic acid molecule, said method comprising amplifying said test nucleic acid molecule and incorporating uracil residues, subjecting the test amplified nucleic acid molecule to uracil specific cleavage mediated by a uracil-N-glycosylase to generate oligonucleotide fragments of from about 2 to about 1000 bases, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

The method of the present invention is predicated in part on the fact that any oligonucleotide fragment differing in nucleotide composition between mutant and wild-type (or reference) sequences will be detected. The method has advantages over previously employed techniques and such advantages include the absence of a gel electrophoresis step thereby reducing time, expertise and need for separation equipment and the lack of dependence on toxic chemicals, such as osmium tetroxide. Whilst the present invention extends to the use of such chemicals in base specific cleavage reactions, it is preferred to use an enzymatic reaction to cleavage the target nucleic acid molecule.

The method of the present invention is particularly useful in detecting previously unknown mutations. This is important as a screening mechanism for inherited diseases and cancers such as during pre-natal diagnosis, diagnosis of a suspected disease or screening for carriers of disease alleles. It also has applications in polymorphism analysis of populations and in studies of evolution, drug resistance, virulence or attenuation of disease agents such as bacteria, viruses or protozoa.

The method may be carried out simultaneously or sequentially with an analysis of a reference to wild-type nucleic acid molecule. Both the test and reference nucleic acid molecules can then be compared. Alternatively, the wild-type nucleic acid molecule may already have been analysed. Conveniently, this information may be stored electronically and upon completion of the analysis of the test nucleic acid molecule, both the test and reference sequences may then be compared manually, electronically or by a computer assisted means.

The method of the present invention may also be used to determine the nucleotide sequence of a nucleic acid molecule.

The nucleotide sequence may be completely determined or a partial sequence obtained for example, for selected nucleotides. The method of the present invention, therefore, permits the rapid determination of a nucleotide sequence which will be invaluable, for example, in the efficient analysis of mutations.

The method of the present invention may be semi or fully automated and the present invention extends to apparatuses for automating the mutation detection assay. The apparatus may also be electronically controlled by a computer programme to facilitate the automation and/or analysis process.

Accordingly, another aspect of the present invention contemplates a computer programme capable of controlling a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Yet another aspect of the present invention is directed to an apparatus capable of detecting a difference of one or more nucleotides between a nucleic acid molecule to be tested and a reference nucleic acid molecule, said apparatus comprising means of subjecting the test nucleic acid molecule to base specific cleavage to generate oligonucleotide fragments, separating the resulting oligonucleotide fragments based on mass by MALDI-TOF MS or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

In a particularly preferred embodiment, the method of apparatus of the present invention also employs a further fragment separation means such as but not limited to post source decay (PSD). PSD, for example, uses the dissociation of highly energised ions during their flight to the detector creating a second dimension. The ions are directed into an electric field of opposite polarity and are reflected. Smaller ions are reflected earlier and reach the detector first. As the spectrum from the decay is dependent on the nucleotide sequence of an oligonucleotide rather than the nucleotide composition, this avoids missing mutations in an oligonucleotide having the same nucleotide composition as a reference oligonucleotide. Although PSD is one convenient fragment separation means, the present invention extends to other similar techniques to separate fragmentation products. Generally these techniques are based on mass although may also be based on electrophoretic mobility, base size, base charge, base paring or other suitable criteria Accordingly, another aspect of the present invention provides a method of detecting a difference of one or more nucleotides between a nucleic acid molecule to be tested and a reference nucleic acid molecule, said method comprising subjecting the test nucleic acid molecule to base specific cleavage to generate oligonucleotide fragments, separating the resulting oligonucleotide fragments based on mass by MALDI-TOF MS and/or other equivalent procedure and subjecting said separated fragments to further separation means to generate a spectrum dependent on nucleotide sequence and then identifying an altered peak relative to a reference nucleic acid molecule subjected to the same procedure wherein the presence of an altered peak is indicative of a difference of one or more nucleotides in said tested nucleic acid molecule.

The MALDI-TOF MS analysis and further separation means may be done sequentially or simultaneously.

Preferably, the further separation means includes or comprises PSD or other similar techniques to separate fragmentation products.

The present invention is particularly useful in identifying and/or locating mutants in heterozygotes. Mutations are detectable on both strains or on one strand only.

Yet another aspect of the present invention provides a method for identifying and/or locating a mutation in one or more bases in a target nucleic acid molecule, subjecting the test nucleic acid molecule to base specific cleavage to generate oligonucleotide fragments, separating the resulting oligonucleotide fragments based on mass by MALDI-TOF MS and/or other equivalent procedure to produce a fingerprint of the oligonucleotide fragments comprising one or more peaks wherein a peak represents the mass of each fragment and identifying an altered peak relative to a reference nucleic acid molecule subjected to the same procedure wherein the presence of an altered peak is indicative of a difference of one or more nucleotides in said tested nucleic acid molecule.

Preferably, the separated fragments are subjected to further separation means such as but not limited to PSD.

The present invention is further described by the following non-limiting Examples.

EXAMPLE 1

Oligonucleotides

Two test 22 mers oligonucleotides with two bases different were used in this study
CCT CAT UTT TTU TTG TAA GAG G [SEQ ID NO:1]
CCT CGT UTT TTU TTG TUA GAG G [SEQ ID NO:2]
The different bases are shown in bold.

For the detection of point mutations (see Example 7), the following oligonucleotides are used:
TUB:
GGT GAC CTG AAC CAC CTC GTG CGT CCA GCC GTT CGT GGC TGT CCA GTC CGC GAAC TCT GAC CTG CGC AAG [SEQ ID NO:3]
TUB-M:
GGT GAC CTG AAC CAC CTC GTG CGT CCA GCC GTT CGA GGC TGT CGA GTC CGCGAA CTC TGA CCT GCG CAA G [SEQ ID NO:4]
TUB-F:
GGT GAC CTG AAC CAC CTC GT [SEQ ID NO:5]
TUB-R:
CTT GCG CAG GTC AGA GTT [SEQ ID NO:6]

TUB and TUB-M are used as template DNA and differ at three residues, bolded above, which comprise two point mutations and one insertion (bracketed and bolded). TUB-F and TUB-R are the "reverse" and "forward" primers used to amplify either TUB or TUB-M in a polymerase chain reaction.

EXAMPLE 2

Cleavage Reaction

The cleavage reactions were carried out using 100 pmol of oligonucleotide, 0.5 units uracil-N-glycoslyase (Perkin-Elmer) 1×PCR buffer (50 mM KCl, 10 mM Tris-HCl pH 8.3) (Perkin-Elmer) in a 250 µl reaction. The reaction mixture was incubated at 50° C. for 20 minutes to allow cleavage of the N-glycosidic bond at uracil. It was then heated for 15 minutes to 105° C. to allow degradation of the phosphate bonds at the basic sites. The mixture was then purified using anion exchange resin to remove buffer salts and other impurities.

EXAMPLE 3

Sample Purification

Qiagen Anion Exchange Resin was equilibrated in 5 mM $NH_4HCO_3$ (Sigma) pH 8.4 (sodium free). 40 µl of the slurry was added to the reaction mixture and the DNA was allowed to bind at room temperature for 5 minutes with gentle shaking. The beads were spun down in a bench centrifuge and the supernatant discarded. The beads were then washed with 3×100 µl volumes of 5 mM $NH_4HCO_3$ pH 8.4 (sodium free) with incubation and centrifugation between each wash. The supernatant was discarded each time. The DNA fragments were then eluted using two 40 µl volumes of 0.5M $NH_4HCO_3$ pH 8.0 (sodium free), with incubation and centrifugation as before but with the supernatant being kept. The supernatant was then evaporated to dryness on a Savant Speedivac and resuspended twice in 20 µl distilled water and evaporated to dryness to remove any residual $NH_4HCO_3$. The final product was resuspended in 5 µl distilled water. The final concentration being approximately 20 pmol/µl.

EXAMPLE 4

The Polymerase Chain Reactions and DNA Uracil Glycosylase Reaction

20 µl reactions were set up containing 2.5 mM $MgCl_2$, 2.5 mM dATP, dCTP, dGTP, 5 mM dUTP, 0.5U Taq Gold (Perkin Elmer), 1.5 mM each TUB-F and TUB-R oligonucleotides and 2.4 fg or either TUB or TUB-M or a mix of both. PCR assays were incubated at 95° C. for 15 minutes then cycled at 95° C.—15 seconds, 60° C.—35 seconds, 72° C.—35 seconds for 40 cycles. PCR reactions were pooled, each pool contained either 10 or 100 PCR reactions. Uracil DNA glycosylase (Perkin Elmer) was added at a ratio of 1U per 10 PCR reactions. Completeness of digestion was confirmed by agarose gel electrophoresis.

EXAMPLE 5

Purification of Digested PCR Products

Each DNA glycosylase reaction was loaded onto a C8 aquapore RP300 column equilibrated with 0.1M TEAA, the column washed with 0.1M TEAA at a flow rate of 0.5 ml/min and elute with 0.1M TEAA in 60% v/v $CH_3CN$. Peaks were collected. Column eluates were desiccated on a Savant Speedivac, evaporative centrifuge, resuspended in water to the original volume and redessicated. Pellets were resuspended in 5 ml $H_2O$. Mass spectrometric samples were prepared as described in Example 6.

EXAMPLE 6

Mass Analysis

3-Hydroxypicolinic acid is prepared at a concentration of 75 mg/ml in 1:1 acetonitrile and water and stored at room temperature in a closed vial in the dark. A new matrix solution is prepared weekly. Cation exchange beads (Bio-Rad 50W-X4, mesh size 100–200 µm) in ammonium form were used to reduce interference from sodium and potassium adducts (Nordhoff et al, 1992). Samples were prepared as follows: 0.5 µl matrix, 0.5 µl sample (10 pmol DNA) and 0.5 µl cation exchange resin were mixed on the slide and allowed to dry. The beads were then blown off with nitrogen gas. Samples were then analysed immediately.

Samples were run on the Kratos Kompact MALDI 4 with 337 nm laser or a Perspective Voyager MALDITOF machine. Linear negative mode was used for all spectra. Fifty shots were fired at power setting 70 to find a sweet so and then a further 50 shots were fired at the sweet spot to obtain the spectrum.

EXAMPLE 7

Simulation

In order to assess the ability of this technique to detect mutations, a computer simulation was designed. Two different stimulations were conducted, one that models a mutation occurring in a haploid genome and the other modelling a mutation occurring in a diploid genome on the background of a wildtype sequence.

In order to optimise the detection of mutations, four separate base specific cleavage reactions have been performed using separated forward and reverse strands and two different base specific reagents, in this case, thymidine and cytosine. A random library of exonic sequences has been extracted from Genbank. This comprises 100,000 kb of coding sequence concatenated into one file. Sequence strings of incremental length are removed from this file. A fingerprint for each strand is generated. This is calculated by generating the sets of post cleavage fragments for each base-specific reagent and sorting the non-redundant fragments. Mutant sequences are created by mutating every residue in the wild-type sequence to each of three possible alternatives. The fingerprint of each mutant is generated and compared to the wild-type fingerprints. If the fingerprints are different, it is recorded as a successful detection and the next mutant examined. If the first base specific cleavage reaction is unable to detect the mutation on the forward strand, the reverse strand is tried and so on until the reverse strand of the second reagent fails. This represents the total failure rate under the described conditions. Conceivably one could increase the power of the technique by using all four base specific reagents on both strands.

EXAMPLE 8

Detection of Base Mutations

Overlaid tracings from the mass spectrogram are presented in FIG. 1. These show the cleavage products of two oligonucleotides 1 and 2 [SEQ ID NO:1 and SEQ ID NO:2, respectively], which differ at two nucleotides, one producing a fragment with a different nucleotide composition and the other introducing a new cleavage site. The new fragments resulting from these differences are easily separate& This example, observed masses deviate from calculated by ±0.02–1%. This is sufficient to assign the correct base composition in this case, however, it is not sufficient to blindly assign base composition peaks from a sample of unknown sequence. A study has been done which concluded that all base compositions can be uniquely specified up to the 14 mer level if one base has a known composition (ie. G=1 in the case of the study, or in our case, T=0) with a measurement of mass to within ±0.01%. This is presently achievable, dependent on the mass analyser used and the sample quality and quantity (Pomerantz et al. 1993).

Base specific cleavage and mass spectrometry is, therefore, able to differentiate between two identical length oligonucleotides with different nucleotide compositions and hence is able to differentiate between two sequences differing at one base (Table 1). Where a mutation changes the residue involved directly in the base specific cleavage reaction (a "U" residue in the case presented here), the difference in size of the resultant products is marked (Table 1). The accuracy of mass determination allows deduction of the base composition of each fragment and therefore, where the sequence is known, will enable deduction of the nature of the mutation.

Table 2 presents stimulation date for the haploid genome case and Table 3 presents the stimulation data where a mutation occurs in a diploid organism in the presence of a wild-type copy. These data are presented as cumulative "failure to identify" mutations based on both strands and two base specific cleavage reactions. Therefore, the last column, which is where the "C" reaction was unable to pick the mutation on the complementary strand represents the "total failure rate" of the technique under these conditions.

EXAMPLE 9

Detection of Point Mutations

Figure 2:
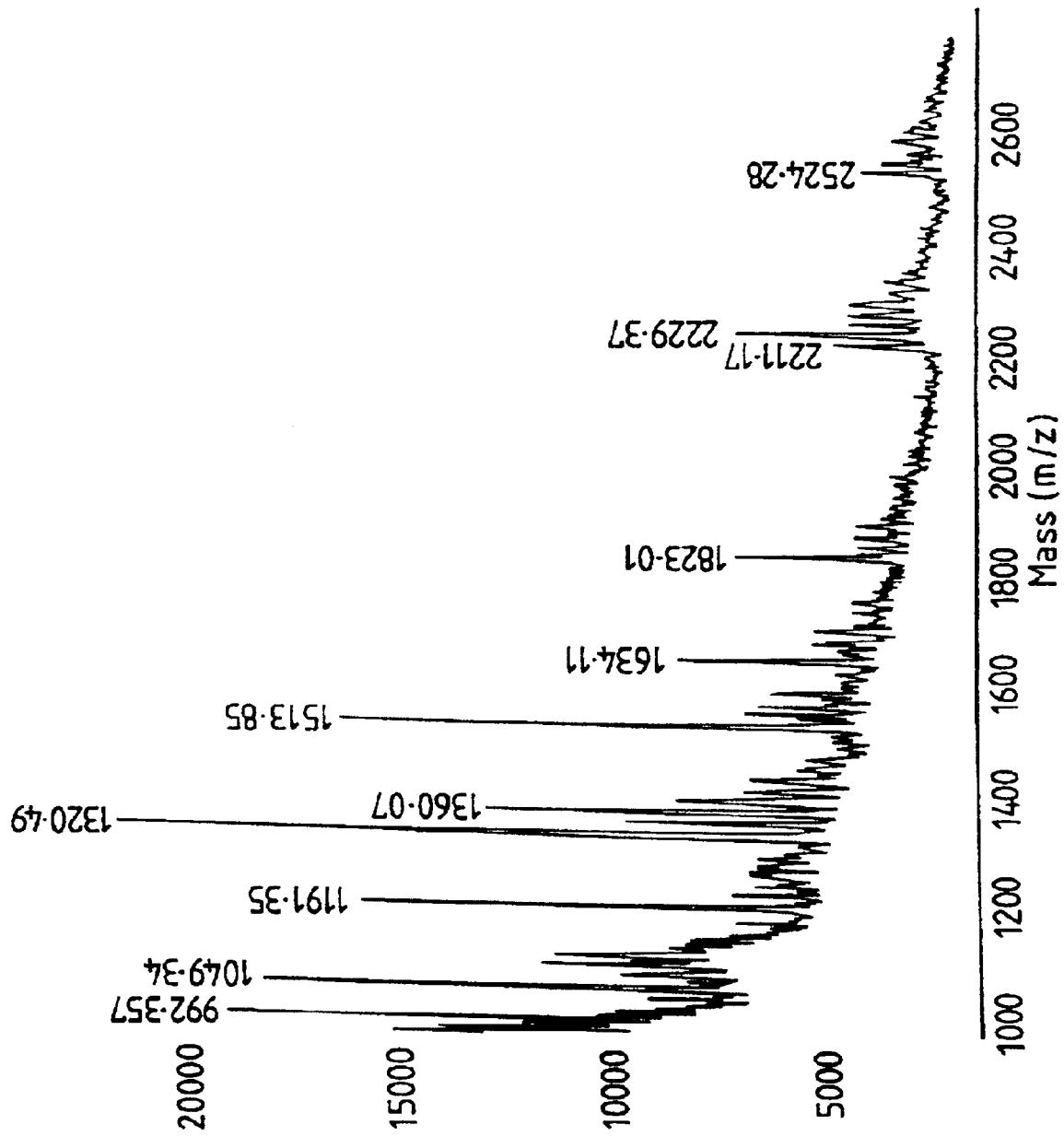
Figure 3:
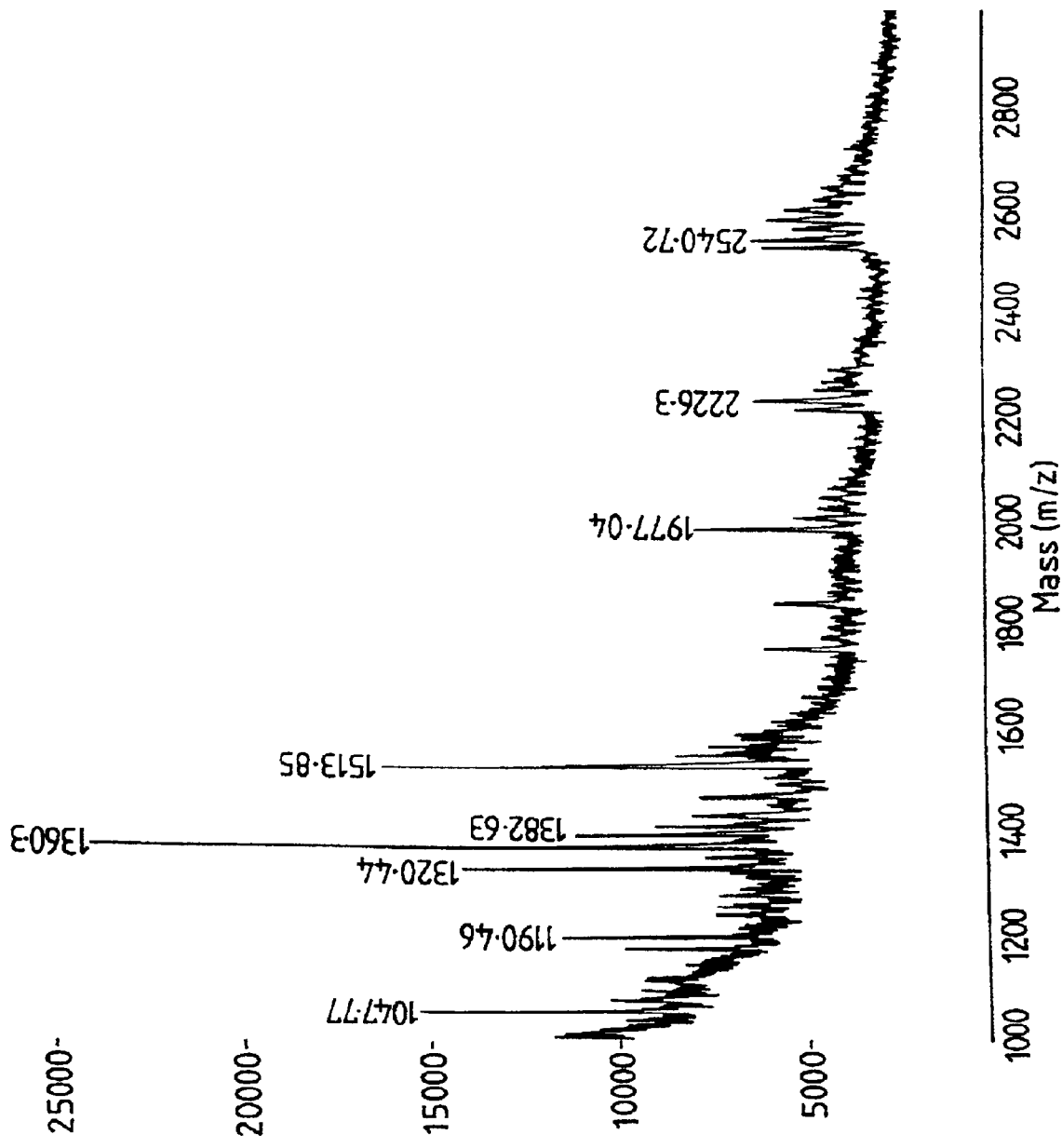
Figure 5A:
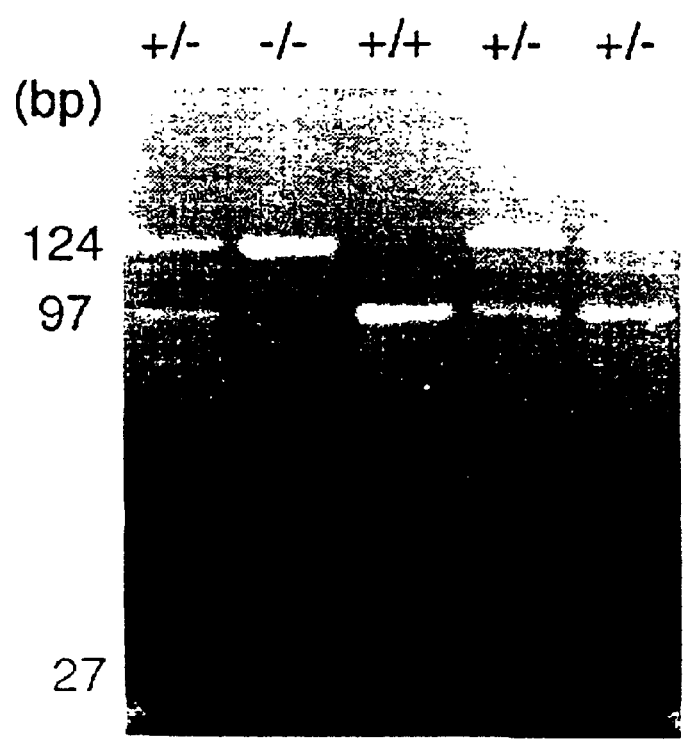
FIG. 5A is a photographic representation of a TaqI restriction digest of IL-12 PCR products from +/− individuals (lanes 1, 4 and 5), a +/+ individual (lane 3) and a −/− individual (lane 2). The 124 bp fragment is cleaved by TaqI (where possible) to produce 97 and 27 bp fragments.

The method of the present invention has been employed on PCR products and is able to detect point mutations and an insertion in DNA that has been amplified using the polymerase chain reaction as discussed below. The PCR templates used, TUB and TUB-M are described in Example 1 and have three differences, two of which are point mutations and the third is an insertion/deletion. All of these differences are visible in the mass spectrograms (FIGS. 2 and 3). FIG. 3 represents the reacted, separated products of both TUB-M and TUB. This is a reconstruction of a heterozygote. FIG. 2 is reacted, separated products of TUB, representing, in this case a homozygote normal Table 4 gives the expected masses for each fragment and the corresponding comments on whether they have been seen. All mutations were seen on either both strands or on one strand only.

TABLE 1

| | | calc. mass | obs. mass |
|---|---|---|---|
| oligo 1: cleavage products | | | |
| a | CCTCAT[1] | 1810.2 | 1811.1 |
| b | TTTT | 1315.8 | 1318.4 |
| c | TTGTAAGAGG[2] | 3190.0 | 3190.9 |
| oligo 2: cleavage products | | | |
| a | CCTCGT[3] | 1826.2 | 1828.2 |
| b | TTTT | 1318.8 | 1318.4 |
| c | TTGT | 1343.8 | 1343.5 |
| d | AGAGG[4] | 1635.0 | 1636.3 |

[1]SEQ ID NO: 18
[2]SEQ ID NO: 19
[3]SEQ ID NO: 20
[4]SEQ ID NO: 21

TABLE 2

| Sequence length | Total number wildtype sequences | Total number mutated sequences | Number of "T" forward failures | % "T" forward failures | Number of "T" reverse failures | % "T" reverse failures | Number of "C" forward failures | % "C" forward failures | Number of "C" reverse failures | % "C" reverse failures |
|---|---|---|---|---|---|---|---|---|---|---|
| 40 | 2500 | 300000 | 10569 | 3.52 | 97 | 0.03 | 1 | 0 | | 0 |
| 60 | 1666 | 299880 | 14723 | 4.91 | 237 | 0.08 | 14 | 0 | 1 | 0 |
| 80 | 1250 | 300000 | 18908 | 6.30 | 401 | 0.13 | 26 | 0.01 | | 0 |
| 100 | 1000 | 300000 | 22825 | 7.61 | 653 | 0.22 | 43 | 0.01 | | 0 |

TABLE 2-continued

| Sequence length | Total number wildtype sequences | Total number mutated sequences | Number of "T" forward failures | % "T" forward failures | Number of "T" reverse failures | % "T" reverse failures | Number of "C" forward failures | % "C" forward failures | Number of "C" reverse failures | % "C" reverse failures |
|---|---|---|---|---|---|---|---|---|---|---|
| 120 | 833 | 299880 | 26383 | 8.80 | 931 | 0.31 | 72 | 0.02 | 2 | 0 |
| 140 | 714 | 299880 | 29751 | 9.92 | 1225 | 0.41 | 93 | 0.03 | 8 | 0 |
| 160 | 625 | 300000 | 32644 | 10.88 | 1480 | 0.49 | 145 | 0.05 | 11 | 0 |
| 180 | 555 | 299700 | 35692 | 11.91 | 1955 | 0.65 | 188 | 0.06 | 21 | 0.01 |
| 200 | 500 | 300000 | 38848 | 12.95 | 2356 | 0.79 | 264 | 0.09 | 24 | 0.01 |
| 220 | 454 | 299640 | 40970 | 13.67 | 2828 | 0.94 | 348 | 0.12 | 32 | 0.01 |
| 240 | 416 | 299520 | 43995 | 14.69 | 3449 | 1.15 | 500 | 0.17 | 62 | 0.02 |
| 260 | 384 | 299520 | 46387 | 15.49 | 3923 | 1.31 | 541 | 0.18 | 88 | 0.03 |
| 280 | 357 | 299880 | 48443 | 16.15 | 4386 | 1.46 | 643 | 0.21 | 50 | 0.02 |
| 300 | 333 | 299700 | 50812 | 16.95 | 4904 | 1.64 | 759 | 0.25 | 103 | 0.03 |
| 320 | 312 | 299520 | 52651 | 17.58 | 5700 | 1.90 | 949 | 0.32 | 142 | 0.05 |
| 340 | 294 | 299880 | 54768 | 18.26 | 6130 | 2.04 | 1082 | 0.36 | 155 | 0.05 |
| 360 | 277 | 299160 | 56876 | 19.01 | 6621 | 2.21 | 1221 | 0.41 | 188 | 0.06 |
| 380 | 263 | 299820 | 59231 | 19.76 | 7445 | 2.48 | 1400 | 0.47 | 236 | 0.08 |
| 400 | 250 | 300000 | 60891 | 20.30 | 7906 | 2.64 | 1507 | 0.50 | 240 | 0.08 |
| 1000 | 100 | 300000 | 98902 | 32.97 | 27716 | 9.24 | 10255 | 3.42 | 3798 | 1.27 |

TABLE 3

| Sequence Length | Total number wildtype sequences | Total number mutated sequences | Number of "T" forward failures | % "T" forward failures | Number of "T" reverse failures | % "T" reverse failures | Number of "C" forward failures | % "C" forward failures | Number of "C" reverse failures | % "C" reverse failures |
|---|---|---|---|---|---|---|---|---|---|---|
| 40 | 2500 | 300000 | 120699 | 40 | 39139 | 13 | 11468 | 4 | 3993 | 1 |
| 60 | 1666 | 299880 | 132516 | 44 | 48716 | 16 | 16455 | 5 | 6426 | 2 |
| 80 | 1250 | 300000 | 142523 | 48 | 57790 | 19 | 22043 | 7 | 9600 | 3 |
| 100 | 1000 | 300000 | 150441 | 50 | 65780 | 22 | 27368 | 9 | 12556 | 4 |
| 120 | 833 | 299880 | 156926 | 52 | 73381 | 24 | 32832 | 11 | 16347 | 5 |
| 140 | 714 | 299880 | 163973 | 55 | 81099 | 27 | 38470 | 13 | 20145 | 7 |
| 160 | 625 | 300000 | 169582 | 57 | 87388 | 29 | 43686 | 15 | 23767 | 8 |
| 180 | 555 | 299700 | 173319 | 58 | 92501 | 31 | 48016 | 16 | 27141 | 9 |
| 200 | 500 | 300000 | 178247 | 59 | 98957 | 33 | 53122 | 18 | 30973 | 10 |
| 220 | 454 | 299640 | 181728 | 61 | 103638 | 35 | 57622 | 19 | 34684 | 12 |
| 240 | 416 | 299520 | 184465 | 62 | 107959 | 36 | 62015 | 21 | 38330 | 13 |
| 260 | 384 | 299520 | 188025 | 63 | 112626 | 38 | 65898 | 22 | 41402 | 14 |
| 280 | 357 | 299880 | 191722 | 64 | 117075 | 39 | 70162 | 23 | 45504 | 15 |
| 300 | 333 | 299700 | 194210 | 65 | 120601 | 40 | 73900 | 25 | 48553 | 16 |
| 320 | 312 | 299520 | 196727 | 66 | 124257 | 41 | 77929 | 26 | 51963 | 17 |
| 340 | 294 | 299880 | 199290 | 66 | 127979 | 43 | 81308 | 27 | 54874 | 18 |
| 360 | 277 | 299160 | 200599 | 67 | 131116 | 44 | 84764 | 28 | 58213 | 19 |
| 380 | 263 | 299820 | 203752 | 68 | 134422 | 45 | 87956 | 29 | 60909 | 20 |
| 400 | 250 | 300000 | 205749 | 69 | 137686 | 46 | 91319 | 30 | 64056 | 21 |
| 420 | 238 | 299880 | 207767 | 69 | 140874 | 47 | 94747 | 32 | 67463 | 22 |
| 440 | 227 | 299640 | 209037 | 70 | 143182 | 48 | 96836 | 32 | 69713 | 23 |
| 460 | 217 | 299460 | 210530 | 70 | 145413 | 49 | 99414 | 33 | 71853 | 24 |
| 480 | 208 | 299520 | 212472 | 71 | 147958 | 49 | 102503 | 34 | 74722 | 25 |
| 500 | 200 | 300000 | 214285 | 71 | 149928 | 50 | 104741 | 35 | 77298 | 26 |
| 520 | 192 | 299520 | 215159 | 72 | 152227 | 51 | 107376 | 36 | 79507 | 27 |
| 540 | 185 | 299700 | 215902 | 72 | 153784 | 51 | 109511 | 37 | 81602 | 27 |

TABLE 4

|  | FRAGMENTS NOT SEEN |  |
|---|---|---|
| EXPECTED TUB FRAGMENTS |  |  |
| GGC | 1045.6 |  |
| CCAC | 1198.8 |  |
| CCACA [SEQ ID NO: 22] | 1512* |  |
| CCAG | 1318.8 |  |
| GGAC | 1358.8 |  |
| CCAGCCG [SEQ ID NO: 23] | 2226.4 |  |
| GCGCAAG [SEQ ID NO: 24] | 2210.4 |  |
| GCGCAAGA [SEQ ID NO: 25] | 2523.6* |  |
| CCGCGAAC [SEQ ID NO: 26] | 2539.6 |  |
| GGAGCACGCAGG [SEQ ID NO: 7] | 3880.4 |  |
| CGGCAAGCACCGACAGG [SEQ ID NO: 8] | 5374.4 |  |
| GGTGACCTGAACCACCTCGTGCG [SEQ ID NO: 9] | 5888.8 | PRIMER |
| CAGGCGCTTGAGACTGGACGCGT [SEQ ID NO: 10] | 6258 | PRIMER |
| EXPECTED TUB-M FRAGMENTS |  |  |
| CCAC | 1198.8 | END |
| CGAG | 1358.8 |  |
| GGAC | 1358.8 |  |
| CGAGGC [SEQ ID NO: 27] | 1977.2 |  |

TABLE 4-continued

| | | FRAGMENTS NOT SEEN |
|---|---|---|
| CCAGCCG [SEQ ID NO: 28] | 2226.4 | |
| GCGCAAG [SEQ ID NO: 29] | 2210.4 | |
| CGACAGCC [SEQ ID NO: 30] | 2539.6 | |
| CCGCGAAC [SEQ ID NO: 31] | 2539.6 | |
| CGAACGGC [SEQ ID NO: 32] | 2579.6 | |
| GGAGCACGCAGG [SEQ ID NO: 11] | 3880.4 | |
| GGTGACCTGAACCACCTCGTCG [SEQ ID NO: 12] | 5888.8 | PRIMER |
| CAGGCGCTTGAGACTGGACGCGT [SEQ ID NO: 13] | 6258 | PRIMER |

*Fragments obtained due to the terminal transferase activity of Taq polymerase which results in the addition of a dATP at the 3' end of the PCR product.

EXAMPLE 10

Modification Detection Protocol

The method of Example 8 is employed except DNA polymerase enzymes arm employed with the ability to incorporate both dNTPs and rNTPs. Specific cleavage reactions are performed on PCR products in which one of the nucleotides is substituted for rNTP. This permits the base specific cleavage reactions to be conducted in alkali at high temperature.

EXAMPLE 11

Identification of Mutation Position

The method of Example 8 employs Uracil-N-glycososylase which cleaves DNA at uracil. It is, therefore, a T reaction as uracil is replacing thymidine in the PCR product. In this Example, cleavage occurs at each of other bases so as to create sets of overlapping data to give information about the position of the mutation.

EXAMPLE 12

Determination of Nucleotide Sequence

The method of the present invention is used to determine a nucleotide sequence of a nucleic acid fragment. The method employed is substantially as described in Example 8.

EXAMPLE 13

Detection of Previously Unknown Mutations

The method of the present invention is further demonstrated on a sequence polymorphism in the IL-12 gene. This previously unreported sequence change results in a TaqI RFLP and, therefore, can be followed by enzymatic digestion of PCR products.

Methods

Template DNA was genomic DNA from human volunteers of each possible genotype of the IL-12 polymorphism (ie. +/+, +/−, and −/−, where + is the presence of the Taq restriction site). PCRs were carried out in 20 µl reactions in 192 well plates in a Corbett Thermocycler with the following reaction mixture: 50 mM KCl, 10 mM Tris-HCl pH 8.3, 25 mM $MgCl_2$ 2.5 mM dATP, dCTP and dGTP (Promega), 5 mM dUTP (Boehringer Mannheim GmbH), 0.5U Ampli-Taq Gold (Perkin Elmer), 0.4 µM primers (Bresatec). After an initial 15 min incubation at 95° C., the reactions were cycled 95° C. 15 secs, 58° C. 35 sec, 72° C. 35 sec, for 40 cycles. 7 reactions were pooled for the homozygotes and 9 for the heterozygote. 1 unit of AmpErase Uracil-N-glycosylase (Perkin Elmer) was added to each pool and the reaction incubated at 50° C. for 1 hour, followed by 30 minutes at 105° C. The extend of completion of the cleavage reaction was monitored by the absence of a band on an agarose gel. The cleavage reaction was monitored by the absence of a band on an agarose gel. The cleavage products were purified using reverse phase HPLC on a 100×2.1 mm C8 aquapore RP300 column (Applied Biosystems). The flow rate was 0.5 ml/min and absorbance was monitored at 254 nm. The sample washed with 0.1M triethylaminoacetate (TEAA) and eluted in 0.1M TEAA/60% w/v acetonitrile and the fraction with absorbance at 254 nm was collected and evaporated to dryness using a Savant Speedivac. The residue was resuspended in 100 µl distilled deionised water and evaporated to dryness and then resuspended in 1 µl water. 0.5 µl of this was mixed with 0.5 µl 3-hydroxypicolinic acid (saturated solution in 50% w/v acetonitrile and 0.5 µl $NH_4^+$ ion-exchange beads (BioRad, 50W-X4, mesh size 100–200 µm) on a sample slide. The mass spectrometer used to characterise the reaction products was a Voyager BioSpectrometry Workstation from PerSeptive Biosystems. 128 laser pulses at power 1800 were averaged. Post Source Decay spectra were collected using a Kratos Kompact MALDI4 TOF mass spectrometer with 377 nm laser and a curved field reflector in positive ion mode. Matrix and sample preparation as above. After scanning in linear mode for the sweet spot, the ion gate was set 34.8 Da above and 36.2 Da below the parent ion at 1727.2 Da. 200 profiles at 5 shots per profile were averaged. Spectra were corrected for the curved field.

Genotypes were confirmed by demonstrating the presence or absence of the TaqI restriction site by digesting PCR products with TaqI restriction enzyme (Gibco-BRL) and analysing the products by agarose electrophoresis. DNA bands were stained with ethidium bromide.

A computer simulation of the method has been written and 100 kb of random coding sequence from Genbank has been fed into it. The program takes discrete-length bites of sequence from a file of concatenated cDNA sequence from Genbank. Each base is mutated to each hypothetical variant of the original sequence by removing the cleaved base leaving the residual short strings. The mass spectrometry was modelled, fragments of different nucleotide composition being distinguishable and those of identical composition being indistinguishable. As quantitation is difficult on the MALDI, changes in peak height was not used as an indication of a change in underlying sequence. The program then compares "spectra" and tallies the number of mutations that were missed. The program can model the detection of a mutation in the presence of a wild-type sequence (heterozygote) or can model the differences between two homozygotes. In the first case a mutation can only be detected by the presence of a new peak and in the latter case, as well as the presence of a new peak, the disappearance of a peak can also signal a change. All four base specific cleavage reactions were used and reactions were performed on separated strands giving a total of 8 reactions per PCR product. Also the model has been refined to take account of the ability of post source decay (PSD) to identify changes in peaks containing a complex mix of oligonucleotides. In this case fragments of different sequence are distinguishable.

Results

A PCR assay was designed to incorporate the mutated region and then subjected to uracil-N-glycosylase treatment.

The products were purified and analysed by MALDI-TOF mass spectrometry. The sequence of the PCR primers and product along with the mutation are shown in FIG. 4. The C to T change gives rise to a Taq RFLP and this can be seen in homozygote and heterozygote state in FIGS. 5A–5G. The spectra generated by the MALDI-TOF can also be seen in FIGS. 5A–5G. The expected and observed masses of the cleavage products from the two alleles are given in Table 5. The position of the mutation and deduction of the changed base is evident from study of this Table.

A limitation to the sensitivity of this method results from the lack of quantitative data available from the MALDI. When the fragment derived from the mutated sequence coincides with other fragments of identical nucleotide composition in the wild-type sequence, its disappearance will go undetected. Similarly, the appearance of a new fragment in the mutated sequence will go unnoticed of it has identical nucleotide composition to one or more other cleavage products. If both these conditions exist for all cleavage reactions, then the mutation will be missed. This technique, therefore, is not as advantageous for longer fragment as for small fragments.

To address this problem, the inventors employed a second dimension detection protocol on the MALDI-TOF machine. Post source decay (PSD) uses the dissociation of the highly energised ions during their flight to the detector as this second dimension. They are directed into an electric field of opposite polarity and are reflected. The smaller ions are reflected earlier and reach the detector first. As the spectrum from the decay is dependent on the sequence of the oligonucleotide (and not the nucleotide composition), the aforementioned limitation is bypassed, generating a method of mutation detection that is now extremely sensitive.

Figure 6A:
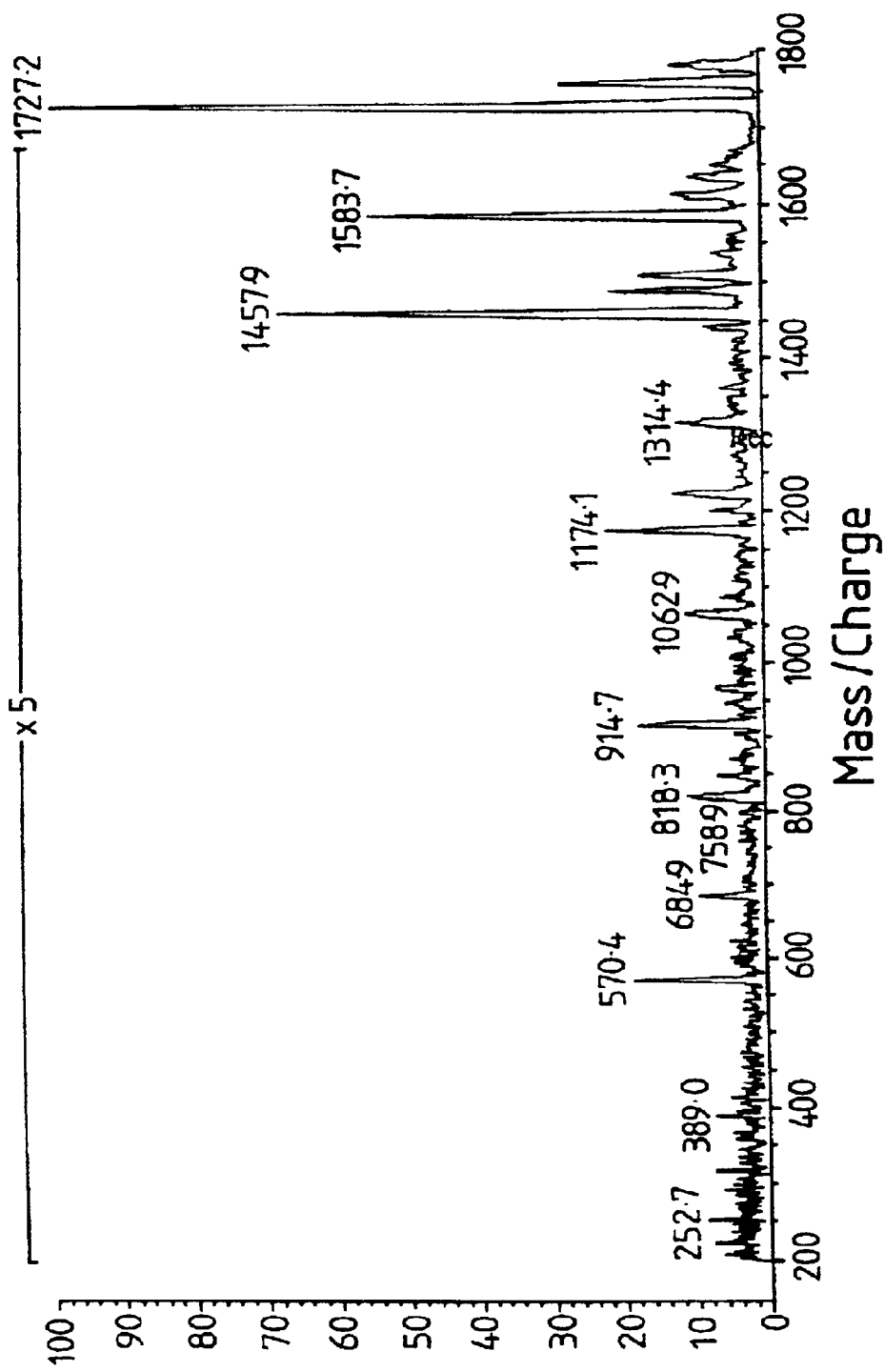
FIGS. 6A—6B are graphical representations of the mass spectrum analysed using post source decay (PSD) on a MALDI-TOF instrument. Spectrum 6A is a 6 mer of sequence CATCCT (SEQ ID NO:16) and spectrum 6B is a 6mer of sequence CACCT (SEQ ID NO:17). Both have parent ion mass of 1727.2 Da. Observed masses are shown above the peaks. PSD fragments are shown at an intensity magnification of five.
Figure 6B:
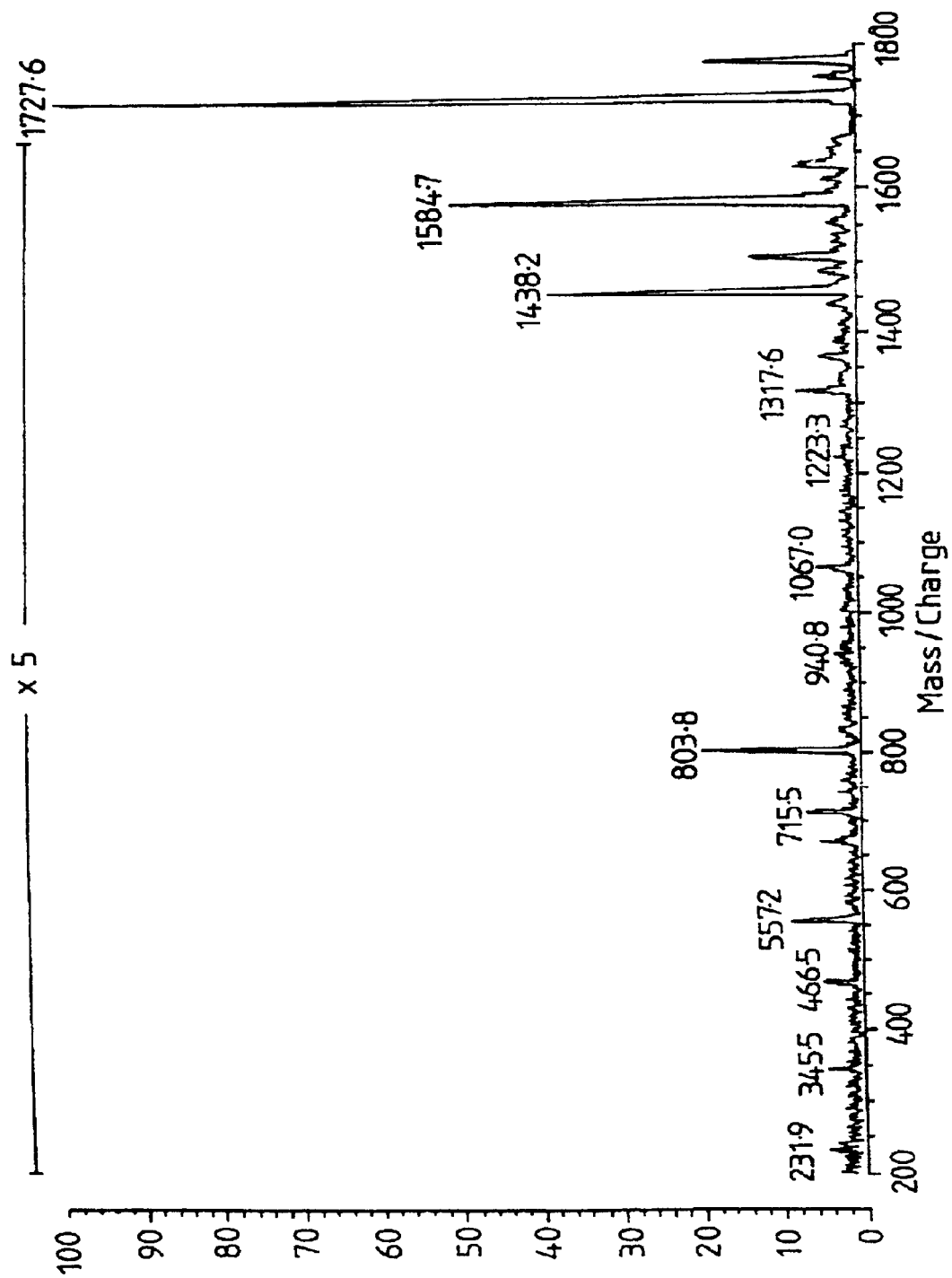

The utility of MALDI-TOF analysis with PSD is demonstrated in FIGS. 6A–6B where two oligonucleotides of identical nucleotide composition are separated by MALDI-TOF using PSD. The resulting spectra are quite distinguishable. Sequence determination of small oligonucleotides is feasible using molecular dissociation methods and, therefore, the subject method extrapolates into an accurate resequencing protocol.

A computer simulation of data from the linear separation of cleavage products has been written. Using Genbank data, the expected number of base substitution that would be identified when comparing two homozygotes over a 250 bp PCR distance is 98.5%. The comparable figure is 95% when a homozygote is compared to a heterozygote. If each mass peak from a base specific cleavage is analysed using a secondary dissociation technique, eg. PSD on the MALDI-TOF machine, then sensitivity of mutation detection improves dramatically. This has also been simulated and for a 1000 bp fragment subjected to base specific cleavage, and analysed with PSD, 99% of all substitutions will be detected for a homozygote to heterozygote comparison and 99.8% when two homozygotes are compared.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A method of detecting a difference of one or more nucleotides between a nucleic acid molecule to be tested and a reference nucleic acid molecule wherein the location of said one or more nucleotide that are different between the nucleic acid molecule to be tested and the reference nucleic acid molecule is unknown , said method comprising subjecting the test nucleic acid molecule to single-base-specific cleavage to generate oligonucleotide fragments, separating the resulting oligonucleotide fragments based on mass by MALDI-TOF MS to produce a fingerprint of the oligonucleotide fragments comprising one or more peaks wherein a peak represents the mass of each fragment and identifying an altered peak relative to said reference nucleic acid molecule subjected to the same procedure wherein the presence of an altered peak is indicative of a difference of one or more nucleotides in said tested nucleic acid molecule relative to said reference nucleic acid molecule.

2. A method according to claim 1 wherein the nucleic acid molecule to be tested is amplified by a polymerase chain reaction (PCR) prior to base specific cleavage.

3. A method according to claim 1 wherein the base specific cleavage results in oligonucleotide fragments of from about 2 bases to about 1000 bases.

4. A method according to claim 3 wherein the base specific cleavage results in oligonucleotide fragments of from about 3 bases to about 500 bases.

5. A method according to claim 4 wherein the base specific cleavage results in oligonucleotide fragments of from about 4 bases to about 100 bases.

6. A method according to claim 1 wherein the base specific cleavage is uracil specific cleavage.

7. A method according to claim 6 wherein the uracil specific cleavage is mediated by uracil-N-glycosylase.

8. A method according to claim 1 further comprising subjecting fragmentation products to further separation (PSD) to generate a spectrum from decay dependent on the nucleotide sequence of the oligonucleotide.

9. A method according to claim 8 wherein the further separation of fragmentation products is by post source decay (PSD).

10. A method for identifying or locating a mutation in one or more bases in a target nucleic acid molecule wherein the location of said mutation within the target nucleic acid molecule is unknown, comprising subjecting the target nucleic acid molecule to single-base-specific cleavage to generate oligonucleotide fragments, separating the resulting olignucleotide fragments based on mass by MALDI-TOF MS to produce a fingerprint of the oligonucleotide fragments comprising one or more peaks wherein a peak represents the mass of each fragment, and identifying an altered peak relative to said reference nucleic acid molecule subjected to the same procedure, wherein the presence of an altered peak is indicative of a mutation in one or more bases in said target nucleic acid molecule relative to said reference nucleic acid molecule.

11. A method according to claim 10 wherein the nucleic acid to be tested is amplified by a polymerase chain reaction (PCR) prior to base specific cleavage.

12. A method according to claim 10 wherein the base specific cleavage results in oligonucleotide fragments of from about 2 bases to about 1000 bases.

13. A method according to claim 12 wherein the base specific cleavage results in oligonucleotide fragments of from about 3 bases to about 500 bases.

14. A method according to claim 13 wherein the base specific cleavage results in oligonucleotide fragments of from about 4 bases to about 100 bases.

15. A method according to claim 10 wherein the base specific cleavage is uracil specific cleavage.

16. A method according to claim 15 wherein the uracil specific cleavage is mediated by uracil-N-glycosylase.

17. A method according to claim 10 further comprising subjecting the oligonucleotide fragments to further separation to generate a spectrum from decay dependent on the nucleotide sequence of the oligonucleotide.

18. A method according to claim 17 wherein the further separation of fragmentation products is by post source decay (PSD).

19. A method of detecting a difference of one or more nucleotides between a nucleic acid molecule acid molecule to be tested and a reference nucleic acid molecule wherein the location of said one or more nucleotides that are different between the nucleic acid molecule to be tested and the reference nucleic acid molecule is unknown, said method comprising subjecting the test molecule to single-base-specific cleavage to generate oligonucleotide fragments, separating the resulting oligonucleotide fragments based on mass by MALDI-TOF MS to produce a fingerprint of the oligonucleotide fragments comprising one or more peaks wherein a peak represents the mass of each fragment, and identifying an altered peak relative to said reference nucleic acid molecule subjected to the same procedure, wherein the presence of an altered peak is indicative of said difference of one or more nucleotdies in said tested nucleic acid molecule relative to said reference nucleic acid molecule, and wherein the difference does not result in a change of a cleavage site.

20. A method for identifying or locating a mutation in one or more bases in a target nucleic acid molecule wherein the mutation does not result in a charge of a cleavage site by a restriction enzyme and wherein the location of said mutation within the target nucleic acid molecule is unknown, comprising subjecting the target nucleic acid molecule to single-base-specific cleavage to generate oligonucleotide fragments, separating the resulting oligonucleotides fragments based on mass by MALDI-TOF MS to produce a fingerprint of the oligonucleotide fragments comprising one or more peaks wherein a peak represents the mass of each fragment, and identifying an altered peak relative to a reference nucleic acid molecule subjected to the same procedure, wherein the presence of an altered peak is indicative of a mutation in one or more bases in said target nucleic acid molecule relative to said reference nucleic acid molecule, and wherein the difference does not result in a change of a cleavage site by a restriction enzyme.

* * * * *

SEQUENCE LISTING

<160> NUMBER OF SEQ ID NOS: 32

<210> SEQ ID NO 1
<211> LENGTH: 22
<212> TYPE: DNA
<213> ORGANISM: artificial sequence
<220> FEATURE:
<223> OTHER INFORMATION: synthetic nucleic acid
<220> FEATURE:
<221> NAME/KEY: misc_feature
<222> LOCATION: (7)..(7)
<223> OTHER INFORMATION: n is uracil
<220> FEATURE:
<221> NAME/KEY: misc_feature
<222> LOCATION: (12)..(12)
<223> OTHER INFORMATION: n is uracil

<400> SEQUENCE: 1
cctcatnttt tnttgtaaga gg                                            22

<210> SEQ ID NO 2
<211> LENGTH: 22
<212> TYPE: DNA
<213> ORGANISM: artificial sequence
<220> FEATURE:
<223> OTHER INFORMATION: synthetic nucleic acid
<220> FEATURE:
<221> NAME/KEY: misc_feature
<222> LOCATION: (7)..(7)
<223> OTHER INFORMATION: n is uracil

```
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (17)..(17)
<223> OTHER INFORMATION: n is uracil

<400> SEQUENCE: 2
cctcgtnttt tnttgtnaga gg                                              22

<210> SEQ ID NO 3
<211> LENGTH: 70
<212> TYPE: DNA
<213> ORGANISM: artificial sequence
<220> FEATURE:
<223> OTHER INFORMATION: synthetic nucleic acid

<400> SEQUENCE: 3
ggtgacctga accacctcgt gcgtccagcc gttcgtggct gtccagtccg caaactctga     60
cctgcgcaag                                                            70

<210> SEQ ID NO 4
<211> LENGTH: 70
<212> TYPE: DNA
<213> ORGANISM: artificial sequence
<220> FEATURE:
<223> OTHER INFORMATION: synthetic nucleic acid

<400> SEQUENCE: 4
ggtgacctga accacctcgt gcgtccagcc gttcgaggct gtcgagtccg cgaactctga     60
cctgcgcaag                                                            70

<210> SEQ ID NO 5
<211> LENGTH: 20
<212> TYPE: DNA
<213> ORGANISM: artificial sequence
<220> FEATURE:
<223> OTHER INFORMATION: synthetic nucleic acid

<400> SEQUENCE: 5
ggtgacctga accacctcgt                                                 20

<210> SEQ ID NO 6
<211> LENGTH: 18
<212> TYPE: DNA
<213> ORGANISM: artificial sequence
<220> FEATURE:
<223> OTHER INFORMATION: synthetic nucleic acid

<400> SEQUENCE: 6
cttgcgcagg tcagagtt                                                   18

<210> SEQ ID NO 7
<211> LENGTH: 12
<212> TYPE: DNA
<213> ORGANISM: artificial sequence
<220> FEATURE:
<223> OTHER INFORMATION: synthetic nucleic acid

<400> SEQUENCE: 7
ggagcacgca gg                                                         12
```

<210> SEQ ID NO 8
<211> LENGTH: 17
<212> TYPE: DNA
<213> ORGANISM: artificial sequence
<220> FEATURE:
<223> OTHER INFORMATION: synthetic nucleic acid

<400> SEQUENCE: 8
cggcaagcac cgacagg                                                        17

<210> SEQ ID NO 9
<211> LENGTH: 23
<212> TYPE: DNA
<213> ORGANISM: artificial sequence
<220> FEATURE:
<223> OTHER INFORMATION: synthetic nucleic acid

<400> SEQUENCE: 9
ggtgacctga accacctcgt gcg                                                 23

<210> SEQ ID NO 10
<211> LENGTH: 23
<212> TYPE: DNA
<213> ORGANISM: artificial sequence
<220> FEATURE:
<223> OTHER INFORMATION: synthetic nucleic acid

<400> SEQUENCE: 10
caggcgcttg agactggacg cgt                                                 23

<210> SEQ ID NO 11
<211> LENGTH: 12
<212> TYPE: DNA
<213> ORGANISM: artificial sequence
<220> FEATURE:
<223> OTHER INFORMATION: synthetic nucleic acid

<400> SEQUENCE: 11
ggagcacgca gg                                                             12

<210> SEQ ID NO 12
<211> LENGTH: 23
<212> TYPE: DNA
<213> ORGANISM: artificial sequence
<220> FEATURE:
<223> OTHER INFORMATION: synthetic nucleic acid

<400> SEQUENCE: 12
ggtgacctga accacctcgt gcg                                                 23

<210> SEQ ID NO 13
<211> LENGTH: 23
<212> TYPE: DNA
<213> ORGANISM: artificial sequence
<220> FEATURE:
<223> OTHER INFORMATION: synthetic nucleic acid

<400> SEQUENCE: 13
caggcgcttg agactggacg cgt                                                 23

<210> SEQ ID NO 14
<211> LENGTH: 124
<212> TYPE: DNA
<213> ORGANISM: artificial sequence
<220> FEATURE:
<223> OTHER INFORMATION: synthetic nucleic acid

```
-continued

<220> FEATURE:
<221> NAME/KEY: misc_feature
<222> LOCATION: (25)..(25)
<223> OTHER INFORMATION: n is uracil
<220> FEATURE:
<221> NAME/KEY: misc_feature
<222> LOCATION: (28)..(30)
<223> OTHER INFORMATION: n is uracil
<220> FEATURE:
<221> NAME/KEY: misc_feature
<222> LOCATION: (32)..(32)
<223> OTHER INFORMATION: n is uracil
<220> FEATURE:
<221> NAME/KEY: misc_feature
<222> LOCATION: (34)..(34)
<223> OTHER INFORMATION: n is uracil
<220> FEATURE:
<221> NAME/KEY: misc_feature
<222> LOCATION: (36)..(36)
<223> OTHER INFORMATION: n is uracil
<220> FEATURE:
<221> NAME/KEY: misc_feature
<222> LOCATION: (39)..(41)
<223> OTHER INFORMATION: n is uracil
<220> FEATURE:
<221> NAME/KEY: misc_feature
<222> LOCATION: (44)..(46)
<223> OTHER INFORMATION: n is uracil
<220> FEATURE:
<221> NAME/KEY: misc_feature
<222> LOCATION: (53)..(59)
<223> OTHER INFORMATION: n is uracil
<220> FEATURE:
<221> NAME/KEY: misc_feature
<222> LOCATION: (64)..(64)
<223> OTHER INFORMATION: n is uracil
<220> FEATURE:
<221> NAME/KEY: misc_feature
<222> LOCATION: (70)..(70)
<223> OTHER INFORMATION: n is uracil
<220> FEATURE:
<221> NAME/KEY: misc_feature
<222> LOCATION: (73)..(73)
<223> OTHER INFORMATION: n is uracil
<220> FEATURE:
<221> NAME/KEY: misc_feature
<222> LOCATION: (75)..(75)
<223> OTHER INFORMATION: n is uracil
<220> FEATURE:
<221> NAME/KEY: misc_feature
<222> LOCATION: (77)..(79)
<223> OTHER INFORMATION: n is uracil
<220> FEATURE:
<221> NAME/KEY: misc_feature
<222> LOCATION: (82)..(82)
<223> OTHER INFORMATION: n is uracil
<220> FEATURE:
<221> NAME/KEY: misc_feature
<222> LOCATION: (84)..(84)
<223> OTHER INFORMATION: n is uracil
<220> FEATURE:
<221> NAME/KEY: misc_feature
<222> LOCATION: (86)..(88)
<223> OTHER INFORMATION: n is uracil
<220> FEATURE:
<221> NAME/KEY: misc_feature
<222> LOCATION: (90)..(90)
<223> OTHER INFORMATION: n is uracil
<220> FEATURE:
<221> NAME/KEY: misc_feature
<222> LOCATION: (92)..(92)
<223> OTHER INFORMATION: n is uracil
<220> FEATURE:
<221> NAME/KEY: misc_feature
<222> LOCATION: (95)..(96)
<223> OTHER INFORMATION: n is uracil
```

```
<220> FEATURE:
<221> NAME/KEY: misc_feature
<222> LOCATION: (100)..(100)
<223> OTHER INFORMATION: n is uracil
<220> FEATURE:
<221> NAME/KEY: misc_feature
<222> LOCATION: (103)..(103)
<223> OTHER INFORMATION: n is uracil
<220> FEATURE:
<221> NAME/KEY: misc_feature
<222> LOCATION: (107)..(107)
<223> OTHER INFORMATION: n is uracil
<220> FEATURE:
<221> NAME/KEY: misc_feature
<222> LOCATION: (110)..(110)
<223> OTHER INFORMATION: n is uracil
<220> FEATURE:
<221> NAME/KEY: misc_feature
<222> LOCATION: (113)..(114)
<223> OTHER INFORMATION: n is uracil
<220> FEATURE:
<221> NAME/KEY: misc_feature
<222> LOCATION: (122)..(122)
<223> OTHER INFORMATION: n is uracil

<400> SEQUENCE: 14
cacaacggaa tagacccaaa aaganaannn cnancngann ngcnnnaaaa cgnnnnnnna      60
ggancacaan ganancnnng cngnannngn anagnncgan gcnaaangcn canngaaaca     120 anca                                                                  124

<210> SEQ ID NO 15
<211> LENGTH: 124
<212> TYPE: DNA
<213> ORGANISM: artificial sequence
<220> FEATURE:
<223> OTHER INFORMATION: synthetic nucleic acid
<220> FEATURE:
<221> NAME/KEY: misc_feature
<222> LOCATION: (2)..(2)
<223> OTHER INFORMATION: n is uracil
<220> FEATURE:
<221> NAME/KEY: misc_feature
<222> LOCATION: (4)..(5)
<223> OTHER INFORMATION: n is uracil
<220> FEATURE:
<221> NAME/KEY: misc_feature
<222> LOCATION: (9)..(10)
<223> OTHER INFORMATION: n is uracil
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (14)..(14)
<223> OTHER INFORMATION: n is uracil
<220> FEATURE:
<221> NAME/KEY: misc_feature
<222> LOCATION: (18)..(22)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature
<222> LOCATION: (26)..(27)
<223> OTHER INFORMATION: n is uracil
<220> FEATURE:
<221> NAME/KEY: misc_feature
<222> LOCATION: (33)..(33)
<223> OTHER INFORMATION: n is uracil
```

```
<220> FEATURE:
<221> NAME/KEY: misc_feature
<222> LOCATION: (38)..(38)
<223> OTHER INFORMATION: n is uracil
<220> FEATURE:
<221> NAME/KEY: misc_feature
<222> LOCATION: (47)..(50)
<223> OTHER INFORMATION: n is uracil
<220> FEATURE:
<221> NAME/KEY: misc_feature
<222> LOCATION: (60)..(60)
<223> OTHER INFORMATION: n is uracil
<220> FEATURE:
<221> NAME/KEY: misc_feature
<222> LOCATION: (63)..(63)
<223> OTHER INFORMATION: n is uracil
<220> FEATURE:
<221> NAME/KEY: misc_feature
<222> LOCATION: (66)..(66)
<223> OTHER INFORMATION: n is uracil
<220> FEATURE:
<221> NAME/KEY: misc_feature
<222> LOCATION: (68)..(69)
<223> OTHER INFORMATION: n is uracil
<220> FEATURE:
<221> NAME/KEY: misc_feature
<222> LOCATION: (72)..(72)
<223> OTHER INFORMATION: n is uracil
<220> FEATURE:
<221> NAME/KEY: misc_feature
<222> LOCATION: (74)..(74)
<223> OTHER INFORMATION: n is uracil
<220> FEATURE:
<221> NAME/KEY: misc_feature
<222> LOCATION: (85)..(85)
<223> OTHER INFORMATION: n is uracil
<220> FEATURE:
<221> NAME/KEY: misc_feature
<222> LOCATION: (91)..(91)
<223> OTHER INFORMATION: n is uracil
<220> FEATURE:
<221> NAME/KEY: misc_feature
<222> LOCATION: (93)..(93)
<223> OTHER INFORMATION: n is uracil
<220> FEATURE:
<221> NAME/KEY: misc_feature
<222> LOCATION: (99)..(99)
<223> OTHER INFORMATION: n is uracil

<400> SEQUENCE: 15
gngnngccnn ancngggnnn nncnannaaa ganagacnaa acgaaannnn gcaaaaaaan      60
ccnagngnna cnanagaaac gacanaaaca nancaagcna cgatttacga gtaactttgt     120
tagt                                                                 124

<210> SEQ ID NO 16
<211> LENGTH: 6
<212> TYPE: DNA
<213> ORGANISM: artificial sequence
<220> FEATURE:
<223> OTHER INFORMATION: synthetic nucleic acid

<400> SEQUENCE: 16 catcct                                                                 6

<210> SEQ ID NO 17
<211> LENGTH: 6
<212> TYPE: DNA
<213> ORGANISM: artificial sequence
<220> FEATURE:
<223> OTHER INFORMATION: synthetic nucleic acid
```

```
<400> SEQUENCE: 17 cacctt                                                              6

<210> SEQ ID NO 18
<211> LENGTH: 6
<212> TYPE: DNA
<213> ORGANISM: artificial sequence
<220> FEATURE:
<223> OTHER INFORMATION: synthetic nucleic acid

<400> SEQUENCE: 18 cctcat                                                              6

<210> SEQ ID NO 19
<211> LENGTH: 10
<212> TYPE: DNA
<213> ORGANISM: artificial sequence
<220> FEATURE:
<223> OTHER INFORMATION: synthetic nucleic acid

<400> SEQUENCE: 19
ttgtaagagg                                                         10

<210> SEQ ID NO 20
<211> LENGTH: 6
<212> TYPE: DNA
<213> ORGANISM: artificial sequence
<220> FEATURE:
<223> OTHER INFORMATION: synthetic nucleic acid

<400> SEQUENCE: 20 cctcgt                                                              6

<210> SEQ ID NO 21
<211> LENGTH: 5
<212> TYPE: DNA
<213> ORGANISM: artificial sequence
<220> FEATURE:
<223> OTHER INFORMATION: synthetic nucleic acid

<400> SEQUENCE: 21 agagg                                                               5

<210> SEQ ID NO 22
<211> LENGTH: 5
<212> TYPE: DNA
<213> ORGANISM: artificial sequence
<220> FEATURE:
<223> OTHER INFORMATION: synthetic nucleic acid

<400> SEQUENCE: 22 ccaca                                                               5

<210> SEQ ID NO 23
<211> LENGTH: 7
<212> TYPE: DNA
<213> ORGANISM: artificial sequence
<220> FEATURE:
<223> OTHER INFORMATION: synthetic nucleic acid

<400> SEQUENCE: 23 ccagccg                                                             7
```

-continued

```
<210> SEQ ID NO 24
<211> LENGTH: 7
<212> TYPE: DNA
<213> ORGANISM: artificial sequence
<220> FEATURE:
<223> OTHER INFORMATION: synthetic nucleic acid

<400> SEQUENCE: 24 gcgcaag                                                                 7

<210> SEQ ID NO 25
<211> LENGTH: 8
<212> TYPE: DNA
<213> ORGANISM: artificial sequence
<220> FEATURE:
<223> OTHER INFORMATION: synthetic nucleic acid

<400> SEQUENCE: 25 gcgcaaga                                                                8

<210> SEQ ID NO 26
<211> LENGTH: 8
<212> TYPE: DNA
<213> ORGANISM: artificial sequence
<220> FEATURE:
<223> OTHER INFORMATION: synthetic nucleic acid

<400> SEQUENCE: 26 ccgcgaac                                                                8

<210> SEQ ID NO 27
<211> LENGTH: 6
<212> TYPE: DNA
<213> ORGANISM: artificial sequence
<220> FEATURE:
<223> OTHER INFORMATION: synthetic nucleic acid

<400> SEQUENCE: 27 cgaggc                                                                  6

<210> SEQ ID NO 28
<211> LENGTH: 7
<212> TYPE: DNA
<213> ORGANISM: artificial sequence
<220> FEATURE:
<223> OTHER INFORMATION: synthetic nucleic acid

<400> SEQUENCE: 28 ccagccg                                                                 7

<210> SEQ ID NO 29
<211> LENGTH: 7
<212> TYPE: DNA
<213> ORGANISM: artificial sequence
<220> FEATURE:
<223> OTHER INFORMATION: synthetic nucleic acid

<400> SEQUENCE: 29 gcgcaag                                                                 7

<210> SEQ ID NO 30
<211> LENGTH: 8
<212> TYPE: DNA
<213> ORGANISM: artificial sequence
<220> FEATURE:
<223> OTHER INFORMATION: synthetic nucleic acid
```

-continued

```
<400> SEQUENCE: 30 cgacagcc                                                                    8

<210> SEQ ID NO 31
<211> LENGTH: 8
<212> TYPE: DNA
<213> ORGANISM: artificial sequence
<220> FEATURE:
<223> OTHER INFORMATION: synthetic nucleic acid

<400> SEQUENCE: 31 ccgcgaac                                                                    8

<210> SEQ ID NO 32
<211> LENGTH: 8
<212> TYPE: DNA
<213> ORGANISM: artificial sequence
<220> FEATURE:
<223> OTHER INFORMATION: synthetic nucleic acid

<400> SEQUENCE: 32 cgaacggc                                                                    8
```